United States Patent
Nallani et al.

(10) Patent No.: US 10,710,044 B2
(45) Date of Patent: Jul. 14, 2020

(54) TUBULAR AND VESICULAR ARCHITECTURES FORMED FROM POLYMER-LIPID BLENDS AND METHOD FOR FORMING THE SAME

(71) Applicant: NANYANG TECHNOLOGICAL UNIVERSITY, Singapore (SG)

(72) Inventors: Madhavan Nallani, Singapore (SG); Bo Liedberg, Singapore (SG); Atul Parikh, Singapore (SG); Hans-Peter De Hoog, Singapore (SG); Amit Kumar Khan, Singapore (SG); Seng Koon Lim, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 154 days.

(21) Appl. No.: 15/563,465

(22) PCT Filed: Mar. 29, 2016

(86) PCT No.: PCT/SG2016/050152
§ 371 (c)(1),
(2) Date: Sep. 29, 2017

(87) PCT Pub. No.: WO2016/159879
PCT Pub. Date: Oct. 6, 2016

(65) Prior Publication Data
US 2018/0126353 A1 May 10, 2018

(30) Foreign Application Priority Data
Apr. 2, 2015 (SG) .......................... 10201502624W

(51) Int. Cl.
*B01J 13/02* (2006.01)
*A61K 47/10* (2017.01)
(Continued)

(52) U.S. Cl.
CPC ............ *B01J 13/02* (2013.01); *A61K 9/1075* (2013.01); *A61K 9/1273* (2013.01);
(Continued)

(58) Field of Classification Search
None
See application file for complete search history.

(56) References Cited

U.S. PATENT DOCUMENTS

2008/0113031 A1* 5/2008 Moodley .............. A61K 9/5073
424/490
2014/0065234 A1 3/2014 Shum et al.

FOREIGN PATENT DOCUMENTS

EP 2695606 A1 2/2014
WO 2008065451 A2 6/2008

OTHER PUBLICATIONS

The Extended European Search Report and Written Opinion issued in EP 16 77 3578 dated Oct. 1, 2018 (8 pages).
(Continued)

*Primary Examiner* — Jeffrey D Washville
(74) *Attorney, Agent, or Firm* — Acuity Law Group, PC; Michael A. Whittaker

(57) ABSTRACT

The invention relates to self-assembled architectures formed from polymer-lipid blends, and in particular, to tubular and vesicular self-assembled architectures formed from polymer-lipid blends. The invention further relates to a method for forming the tubular and vesicular self-assembled architectures. The invention provides a composition comprising a lipid and an amphiphilic block copolymer, wherein the amphiphilic block copolymer is capable of undergoing self-assembly to form an architecture of a first geometry, wherein the composition undergoes self-assembly to form a bilayer
(Continued)

architecture enclosing a volume of a second geometry, wherein the second geometry is different from that of the first geometry.

8 Claims, 16 Drawing Sheets

(51) Int. Cl.

| | |
|---|---|
| A61K 47/24 | (2006.01) |
| A61K 9/127 | (2006.01) |
| A61K 9/107 | (2006.01) |
| A61K 47/34 | (2017.01) |
| C09B 67/02 | (2006.01) |

(52) U.S. Cl.
CPC .......... *A61K 9/1277* (2013.01); *A61K 9/1278* (2013.01); *A61K 47/10* (2013.01); *A61K 47/24* (2013.01); *A61K 47/34* (2013.01); *C09B 67/0097* (2013.01)

(56) References Cited

OTHER PUBLICATIONS

Adrian et al., Cryoelectron Microscopy of Viruses. Nature. Mar. 1-7, 1984;308(5954):32-36.
Ajo-Franklin et al., Probing the Structure of Supported Membranes and Tethered Oligonucleotides by Fluorescence Interference Contrast Microscopy. Langmuir. May 24, 2005;21(11):4976-4983.
Bangham and Horne, Negative Staining of Phospholipids and their Structural Modification by Surface-active Agents as observed in the Electron Microscope. J Mol Biol. May 1964;8:660-668.
Canham, The Minimum Energy of Bending as a Possible Explanation of the Biconcave Shape of the Human Red Blood Cell. J Theor Biol. Jan. 1970;26(1):61-81.
Dabora and Sheetz, The Microtubule-Dependent Formation of a Tubulovesicular Network with Characteristics of the ER from Cultured Cell Extracts. Cell. Jul. 1, 1988;54(1):27-35.
Degennes, Conformations of Polymers Attached to an Interface. Macromolecules 1980;13(5):1069-1075.
Dennis et al., Phospholipase A2 Enzymes: Physical Structure Biological Function, Disease Implication, Chemical Inhibition, and Therapeutic Intervention. Chem Rev. 2011;111( 10): 6130-6185.
Discher and Ahmed, Polymersomes. Ann Rev Biomed Engineer. Palo Alto, Annual Reviews. 2006;8:323-341.
Discher and Eisenherg, Polymer vesicles. Science 2002;297(5583):967-973.
Discher et al., Polymersomes: Tough vesicles made from diblock copolymers. Science 1999;284(5417): 1143-1146.
Geng et al., Shape effects of filaments versus spherical particles in flow and drug delivery. Nature Nanotechnology, 2007; 2 (4):249-255.
Griffiths and Simons, The Trans Golgi Network-Sorting at the Exit Site of the Golgi-Complex. Science 1986;234(4775):438-443.
Helfrich, Elastic Properties of Lipid Bilayers—Theory and Possible Experiments. Zeilschrift Fur Naturforschung C—a Journal of Biosciences 1973 ;C28( 11-1 ): 693-703.
Koster.et al., Perspectives of molecular and cellular electron tomography. J Structural Biol. 1997;120(3): 276-308.
Kremer et al., Computer Visualization of Three-Dimensional Image Data Using IMOD. J Structural Biol. 1996;116(1): 11-76.
Kugiyama et al., Circulating Levels of Secretory Type II Phospholipase A2 Predict Coronary Events in Patients with Coronary Artery Disease. Circulation 1999;100(12): 1280-1284.
Le Meins et al., Hybrid polymer/lipid vesicles: state of the art and future perspectives. Materials Today, Oct. 2013;16(10):397-402.
Lee and Chen, Dynamic Behavior of Endoplasmic reticulum in Living Cells. Cell 1988;54(1): 37-46.
Lim et al., Hybrid, Nanoscale Phospholipid/Block Copolymer Vesicles. Polymers, Sep. 6, 2013;5(3):1102-1114.
Lin et al., Lipid Asymmetry in DLPC/DSPC-Supported Lipid Bilayers: A Combined AFM and Fluorescence Microscopy Study. Biophysical Journal 2006 ;90(1 ): 228-237.
Lucic et al., Structural studies by electron tomography: From cells to molecules. Annual Review of Biochemistry. Palo Alto Annual Reviews. 2005;74: 833-865.
Marques, Size and Stability of Catanionic Vesicles: Effects of Formation Path, Sonication, and Aging. Langmuir 2000;16(11 ): 4798-4807.
Maxfield and McGraw (2004). Endocytic recycling. Nature Reviews Molecular Cell Biology 2004;5(2): 121-132.
McMahon and Gallop, Membrane curvature and mechanisms of dynamic cell membrane remodelling. Nature 2005; 438(7068): 590-596.
Miao et al., Budding Transitions of Fluid-Bilayer Vesicles—The Effect of Area Difference Elasticity. Physical Review 1994;E49(6): 5389-5407.
Murakami et al., Secreted pbospholipase A2 revisited. J Biochem. 2011;150(3): 233-255.
Nevalainen, Serum phospholipases A2 in inflammatory diseases. Clin Chem. 1993;39 (12): 2453-2459.
Pettersen et al., UCSF Chimera—A visualization system for exploratory research and analysis. J Computational Chem. 2004;25(13): 1605-1612.
Presley et al., ER-to-Golgi transport visualized in living cells. Nature 1997;389(6646): 81-85.
Ramirez and Jain, Phospholipase"A2 at the Bilayer Interface." Proteins-Structure Function and Genetics 1991;9(4): 229-239.
Rodriguez-Garcia et al., Polymersomes: smart vesicles of tunable rigidity and permeability. Soft Matter 2011;7(4): 1532-1542.
Roux et al., A minimal system allowing tubulation with molecular motors pulling on giant liposomes. Proc Nat Acad Sci USA 2002;99(8):5394-5399.
Safran et al., Theory of Spontaneous Vesicle Formation in Surfactant Mixtures. Science 1990;248(4953): 354-356.
Sandstrom et al., Influence of preparation path on the formation of discs and threadlike micelles in DSPE-PEG2000/lipid systems. Biophys Chem. Feb. 2008;132(2-3):97-103.
Scaglione and Rintoul, A fluorescence-quenching assay for measuring permeability of reconstituted lens MIP26. Investigative Ophthalmology & Visual Science 1989;30(5):961-966.
Schneider et al., NIH Image to ImageJ: 25 years of image analysis. Nat Meth 2012;9(7): 671-675.
Sheetz and Singer, Biological Membranes as Bilayer Couples—Molecular Mechanism of Drug-Erythrocyte Interactions. Proc Nat Acad Sci USA 1974;71(11 ): 4457-4461.
Stachowiak et al., A cost-benefit analysis of the physical mechanisms of membrane curvature. Nature Cell Biology 2013;15(9): 1019-1027.
Svetina et al., Lipid Bilayer Elasticity and the Bilayer Couple Interpretation of Red-Cell Shape Transformations and Lysis. Studia Biophysica 1985;110( 1-3): 177-184.
Trucco et al., Secretory traffic triggers the formation of tubular continuities across Golgi sub-compartments. Nature Cell Biol. 2004;6(11 ):1071-U1011.
Weidman et al., Golgi Membrane Dynamics Imaged by Freeze-Etch Electron-Microscopy—Views of Different Membrane Coatings Involved in Tubulation Versus Vesiculation. Cell 1993;75( 1): 123-133.
Zhu et al., Disk-cylinder and disk-sphere nanoparticles via a block copolymer blend solution construction. Nat Commun. 2013;4:2297.
Zimmerberg and Kozlov, How proteins produce cellular membrane curvature. Nature Reviews Molecular Cell Biology 2006;7(1):9-19.
International Search Report issued by the ISA/SG in PCT/SG2016/050152 dated Jun. 13, 2016 (5 pages).
Written Opinion issued by the ISA/SG in PCT/SG2016/050152 dated Jun. 13, 2016 (6 pages).
International Preliminary Report on Patentability issued by the ISA/SG in PCT/SG2016/050152 dated Mar. 16, 2017 (18 pages).

(56) References Cited

OTHER PUBLICATIONS

"Micelle" retrived from https://en.wikipedia.org/w/index.php?title=Micelle&oldid=637792170 on Jan. 14, 2020 (5 pages).

* cited by examiner

50:50

50:50

TUBULAR AND VESICULAR ARCHITECTURES FORMED FROM POLYMER-LIPID BLENDS AND METHOD FOR FORMING THE SAME

CROSS-REFERENCE TO RELATED APPLICATION

The present invention is filed under 35 U.S.C. § 371 as the U.S. national phase of International Application No. PCT/SG2016/050152, filed Mar. 29, 2016, which designated the U.S. and claims the benefit of priority of Singapore Patent Application No. 10201502624W, filed Apr. 2, 2015, the contents of which each being hereby incorporated by reference in its entirety for all purposes.

TECHNICAL FIELD

The invention relates to self-assembled architectures formed from polymer-lipid blends, and in particular, to tubular and vesicular self-assembled architectures formed from polymer-lipid blends. The invention further relates to a method for forming the tubular and vesicular self-assembled architectures.

BACKGROUND

Soft-matter aggregates that can entrap small volumes of water have since long been investigated in delivery of pharmaceuticals (e.g. small molecules, proteins, DNA) to the body. A popular example is vesicles formed from liposomes, which are microscopic hollow spheres where a thin bilayer lipid membrane encloses a volume of water. Although liposomes are potentially well-suited for compound delivery, they suffer from the inherent instability of the thin lipid bilayer membrane. Hence, recently options have been explored in which the amphiphile is not based on lipids, but rather on amphiphilic block or random copolymers or proteins.

Apart from vesicular structures, other self-assembled architectures that can form from lipids or amphiphilic molecules include micellar, sheet-like and tubular architectures. The latter architecture is especially interesting for in-vivo applications since they show characteristic clearance behaviour.

SUMMARY

According to a first aspect of the invention, there is disclosed a composition comprising a lipid and an amphiphilic block copolymer. The amphiphilic block copolymer is capable of undergoing self-assembly to form an architecture of a first geometry. The composition undergoes self-assembly to form a bilayer architecture enclosing a volume of a second geometry, wherein the second geometry is different from that of the first geometry.

According to a second aspect of the invention, there is disclosed a method for forming a composition of the first aspect. The method comprises mixing in a pre-determined molar proportion of a solution of the amphiphilic block copolymer with the lipid in an organic solvent, evaporating the organic solvent after the mixing to obtain a lipid-polymer cake, desiccating the lipid-polymer cake to obtain a dry thin film, rehydrating the dry thin film in a hydrating solution to obtain an emulsion, and extruding the emulsion.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1A:
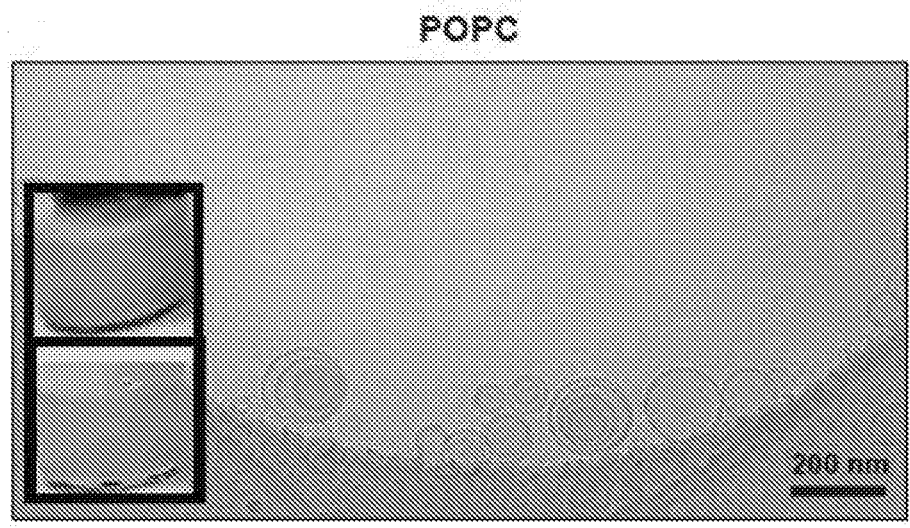
FIG. 1A-1F show cryoEM images of nanostructures formed from thin film rehydration of phospholipid POPC, block copolymer PBD-PEO, and POPC/PBD-PEO mixtures. 1A. POPC; 1B. POPC/PBDPEO (75:25); 1C. POPC/PBD-PEO (50:50); 1D. POPC/PBD-PEO (25:75); 1E, 1F. PBD-PEO; Scale bar is 200 nm. Insets. Photographs showing the difference in macroscopic turbidity of vesicle suspension, depending on vesicle composition. Vesicles formed by rehydration with PBS (top), or labeled with 0.5% Rho-PE (Bottom).
Figure 1B:
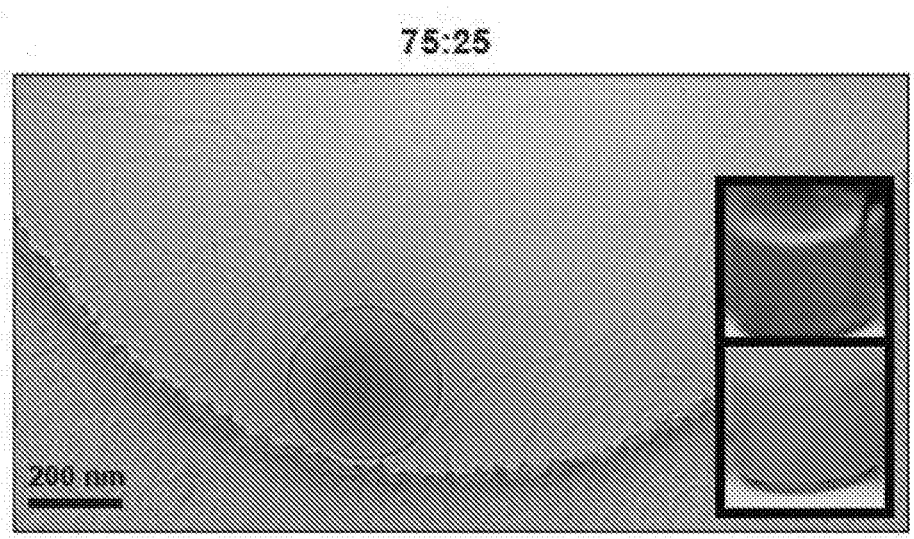
Figure 1C:
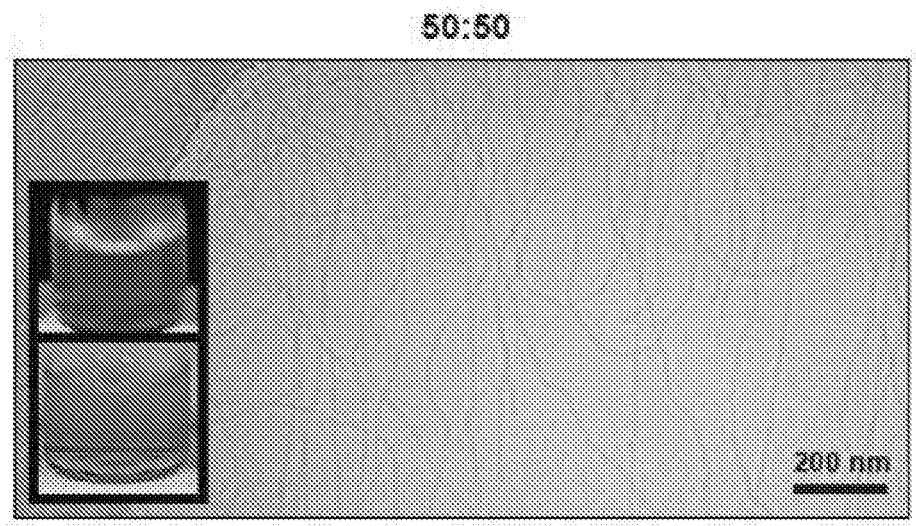
Figure 1D:
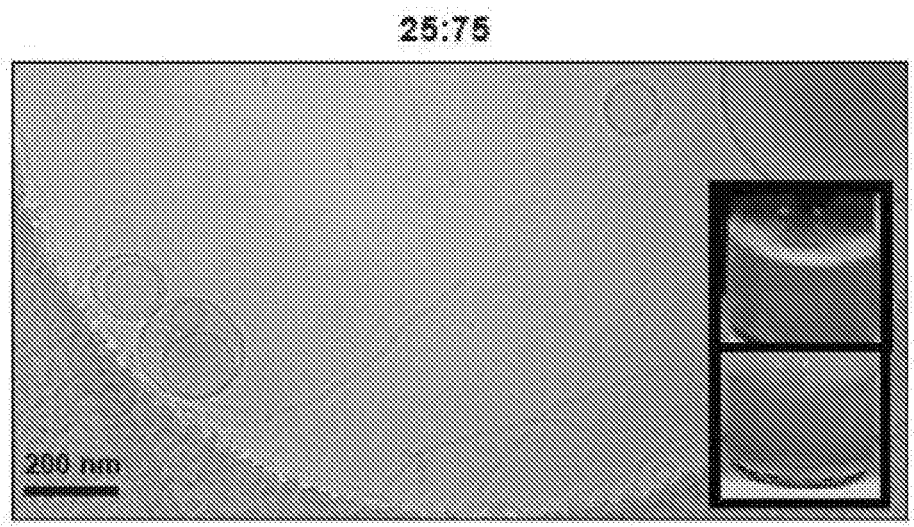
Figure 1E:
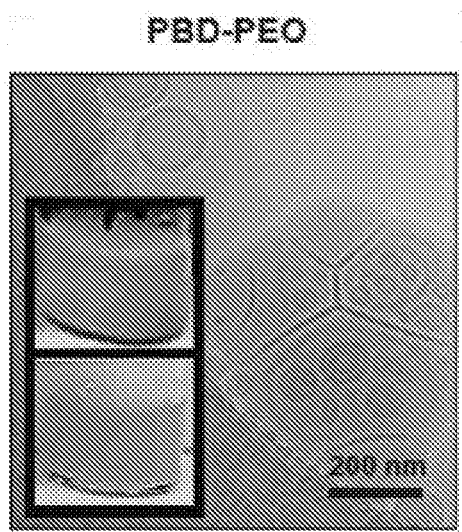

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural and chemical changes may be made without departing from the scope of the invention. The various embodiments are not necessarily mutually exclusive, as some embodiments can be combined with one or more other embodiments to form new embodiments.

Membrane tubules are pervasive in eukaryotic cells. They represent a prominent structural feature of endoplasmic reticulum (ER), in which an elaborate network of interconnected tubules—of conserved diameters (25-100 nm) from yeast to mammalian cells—extends over a large part of the cell. They are also present in Golgi apparatus, possibly playing a role in intracellular trafficking. In addition to these static structures, tubular morphology of membranes also appears transiently in recycling endosomes and as intracellular transport carriers. In all of these cases, curvatures needed to fashion the tubular morphology are thought to emerge through physical-chemical effects, such as scaffolding, crowding, and mechanical forces, which originate from protein (i.e., motor proteins, cytoskeleton) or localized lipid (e.g., enzymatic hydrolysis, spontaneous curvature generation) activity.

Unlike membranes of living cells, in vitro synthetic constructs—consisting of mixtures of amphiphiles of vastly different molecular properties—circumvent the constraints on compositional and/or area asymmetry and open up a thermodynamic window for the spontaneous tubule formation. This is because synthetic amphiphiles can be selected such that they produce requisite "miscibility gap" in membrane composition (SC model) and/or area-difference (BC model) between the two constituent leaflets. Such amphiphilic mixtures then should allow to reconstitute membrane tubules in vitro. To explore this possibility, vesicular microphases formed by the hydration of binary mixtures of a zwitterionic lipid and an amphiphilic diblock polymer are investigated. Structurally, the two amphiphiles differ both in the types of their headgroups as well as the thicknesses of their hydrophobic core. These then give rise to differences in their elastic material properties (e.g. bending rigidity and area compression modulus) as well as in intermolecular head-group interactions. By systematically varying the molar ratios of the two amphiphiles, it is found, by using electron cryo-microscopy (cryoEM) combined with 3D electron tomographic reconstruction, that the aqueous suspension of mixtures of lipids and amphiphilic block copolymer spontaneously generate membrane tubules over a wide range of compositions.

This tendency for tubule formation is most pronounced when the amphiphile composition reaches an equimolar proportion of lipid and polymer. It is confirmed that these tubular mixed lipid-polymer vesicles are indeed stabilized through the creation of a significant miscibility gap using two independent assays. Firstly, a fluorescence quenching assay using cobalt (II) chloride—testing the access to labelled lipids from the extra-tubular space—reveals that the inner, compressed monolayer accumulates greater proportion of lipids and the outer stretched leaflet is enriched in the polymer component. Secondly, it is confirmed compositional asymmetry by monitoring the inhibition in the activity of exogenously introduced phospholipase A2 (PLA2). Because PLA2 can hydrolyze the lipid but not the polymer component of the vesicle, decreased lipase activity in mixed tubular vesicles validates the inaccessibility of the lipid from the outside. Taken together, these observations are consistent with the theoretical prediction that compositional asymmetry resulting from non-ideal mixing—in the present case between lipids and polymers between the two leaflets because of steric factors—can provide an effective means to generate the needed area-difference or the spontaneous bilayer curvature to promote spontaneous formation of tubular vesicles of preferred, nanometre scale diameters.

In various embodiments, it is described a method for a straightforward fabrication of high quantities of hollow soft matter tubes, which is based on the physical separation of amphiphilic block copolymers to the outer shell and of lipids to the inner shell of the bilayer membrane forming the tubes. The tubes solely form when the molar ratio of lipid to polymer is close to 1:1. Because of this configuration the formed dispersions are thermodynamically stable over time and there is little or no presence of other architectures such as micelles or vesicles. The tubes can encapsulate small drug-like molecules and amphiphilic molecules.

Although tubes are ubiquitous in nature (viz. the golgi apparatus), attempts to reliably produce them by synthetic methods have been faced with difficulties. Considering amphiphilic self-assembly, tube formation has been reported using simple lipids. However, these preparations unequivocally need continuous mechanical input or require co-assembly with structural proteins. Some success has been achieved using peptide nanotubes. Their formation is based on the interaction of secondary structure elements in the peptide structure. For in vivo applications, they may be less suitable since the peptidic nature could be immunogenic. The present disclosure reveals examples of tubes with chemically dissimilar inner and outer shells.

After the successful fabrication of tubular architectures, additional polymer-lipid preparations were investigated, where it can be made the observation that the addition of lipids induces an aggregation state (e.g. in terms of a geometry defined by a volume enclosed by the architecture) in the polymer-lipid blend that is different from that of the original polymer. For instance, blends of lipid and PEG-PBD copolymer form tubes, while the copolymer itself forms vesicles. Blends of lipid and a set of biodegradable block copolymers (e.g. PEG-PLA and PEG-PCL) form vesicles, whereas the polymer itself does not form any well-defined aggregates at all.

Thus, according to a first aspect of the disclosure, there is disclosed a composition comprising a lipid and an amphiphilic block copolymer. The amphiphilic block copolymer is capable of undergoing self-assembly to form an architecture of a first geometry. The composition undergoes self-assembly to form a bilayer architecture enclosing a volume of a second geometry, wherein the second geometry is different from that of the first geometry.

Lipids are a group of naturally occurring molecules that include fats, waxes, sterols, fat-soluble vitamins (such as vitamins A, D, E, and K), monoglycerides, diglycerides, triglycerides, phospholipids, and others. The main biological functions of lipids include storing energy, signalling, and acting as structural components of cell membranes.

In various embodiments, the lipid is selected from the group consisting of a phospholipid, a sphingolipid, a sterol, and a mixture thereof.

For example, the lipid may comprise one or more aliphatic tails each comprised of two hydrocarbon chains of 14 to 22 carbon atoms in length, each hydrocarbon chain having varying degree of unsaturation.

In various embodiments, the aliphatic tail is selected from the group consisting of phosphatidyl choline (PC), phosphatidyl ethanolamine (PE), phosphatidic acid (PA), phosphatidyl inositol (PI), sphingomyelin (SM), ceramide (CM), ganglioside (GM), and a mixture thereof.

In one embodiment, the lipid is 1-palmitoyl-2-oleoyl-sn-glycero-3-phosphatidylcholine (POPC).

Amphiphilic block copolymers undergo self-assembly in dilute solutions to form vesicles with a polymeric membrane, which can be of different types such as diblock and triblock. The polymeric vesicles may also be formed of tetrablock or pentablock copolymers. Diblock copolymers self-assemble into bilayers, placing two hydrophobic blocks tail-to-tail. In most cases, the vesicular membrane has an insoluble inner layer and soluble outer layers. The driving force for the polymeric vesicle formation by self-assembly is considered to be the microphase separation of the insoluble blocks, which tend to associate in order to shield themselves from contact with water. The polymeric vesicles possess remarkable properties due to the large molecular weight of the constituent copolymers. Vesicle formation is favoured upon an increase in total molecular weight of the block copolymers. As a consequence, diffusion of the polymeric amphiphiles in these vesicles is very low compared to vesicles formed by lipids and surfactants. Owing to this less mobility of polymer chains aggregated in vesicle structure, it is possible to obtain stable morphologies.

As mentioned above, the amphiphilic block copolymer in itself (i.e. in the absence of the lipid) is capable of undergoing self-assembly to form an architecture of a first geometry. However, in the present context, the amphiphilic block copolymer is purposefully led to undergo self-assembly in the presence of the lipid to form the bilayer architecture enclosing a volume of the second geometry.

In various embodiments, the bilayer architecture comprises an outer layer, wherein the outer layer comprises the amphiphilic block copolymer comprising a hydrophobic polymer segment and a hydrophilic polymer segment. The bilayer architecture further comprises an inner layer, wherein the inner layer comprises the lipid.

In alternative embodiments, the bilayer architecture comprises an outer layer, wherein the outer layer comprises a mixture of the lipid and the amphiphilic block copolymer, wherein the amphiphilic block copolymer comprises a hydrophobic polymer segment and a hydrophilic polymer segment. The bilayer architecture further comprises an inner layer, wherein the inner layer comprises a mixture of the lipid and the amphiphilic block copolymer, wherein the amphiphilic block copolymer comprises a hydrophobic polymer segment and a hydrophilic polymer segment. In other words, the each of the inner and outer layers comprises a mixture of both constituents.

In various embodiments, the amphiphilic block copolymer is selected from the group consisting of diblock or multi-block copolymers of poly(ethylene oxide)-polybutadiene (PEG-PBD), poly(ethylene glycol)-polycaprolactone (PEG-PCL), poly(ethylene glycol)-poly(lactic acid) (PEG-PLA), poly(ethylene glycol)-poly(butylene oxide) (PEG-PBO), poly(ethylene glycol)-poly(propylene oxide) (PEG-PPO), poly(ethylene glycol)-poly(N-isopropyl acrylamide) (PEG-PNIPAM) poly(methyloxazoline)-poly(dimethyl siloxane) (PMOXA-PDMS), poly(ethylene glycol)-polystyrene (PEG-PS), poly(acrylic acid)-polystyrene (PA-PS), poly(trimethylene carbonate)-poly(glutamic acid) (PTC-PGA), poly(trimethylene carbonate)-poly(aspartic acid) (PTC-PAA), poly(lysine)-poly(leucine) (PK-PL), and a mixture thereof.

In preferred embodiments, the amphiphilic block copolymer is PEO-PBD, PEG-PLA or PEG-PCL.

Suitable applications of present architectures include in vivo delivery of pharmaceutical compounds. Another application would be in skin care and wound dressing, the foremost reason being their capacity to stably integrate high amounts of lipids. The segregation of lipids to the inside of the vesicle will protect them from degradation so that subcutaneous penetration is more efficient.

Therefore, in various embodiments, the bilayer architecture further comprises a hydrophobic or lipophilic substance encapsulated within the volume of the second geometry.

For example, the bilayer architecture further comprises a water-soluble substance dissolved in the volume of the second geometry. The substance may be bioactive or pharmaceutically active.

As mentioned above, the second geometry of the bilayer architecture is different from the first geometry formed by the amphiphilic block copolymers in the absence of the lipid. In various examples, the bilayer architecture comprises a tubular geometry while the first geometry may be spherical. In alternative examples, the bilayer architecture comprises a spherical geometry while the first geometry may be tubular.

According to a second aspect of the disclosure, there is disclosed a method for forming a composition of the first aspect. The method comprises mixing in a pre-determined molar proportion of a solution of the amphiphilic block copolymer with the lipid in an organic solvent, evaporating the organic solvent after the mixing to obtain a lipid-polymer cake, desiccating the lipid-polymer cake to obtain a dry thin film, rehydrating the dry thin film in a hydrating solution to obtain an emulsion, and extruding the emulsion.

In various embodiments, the pre-determined molar proportion of amphiphilic block copolymer to lipid is between 0.15:0.85 and 0.85:0.15. For example, the pre-determined molar proportion may be 0.15:0.85, 0.2:0.8, 0.25:0.75, 0.3:0.7, 0.35:0.65, 0.4:0.6, 0.45:0.55, 1:1, 0.55:0.45, 0.6:0.4, 0.65:0.35, 0.7:0.3, 0.75:0.25, 0.8:0.2, 0.85:0.15, and any ratio therebetween.

In preferred embodiments, the pre-determined proportion of amphiphilic block copolymer to lipid is 1:1. At such pre-determined proportion, the thus-formed bilayer architecture has a tubular geometry.

In various embodiments, the organic solvent is selected from the group consisting of chloroform, ethanol, glycerol, tetrahydrofuran, dichloromethane, hexane, heptane, ethyl acetate, acetone, and a mixture thereof.

In one embodiment, the organic solvent is chloroform.

In various embodiments, the organic solvent contains a substance to be integrated in the bilayer architecture.

In various embodiments, the hydrating solution is selected from the group consisting of phosphate-buffered saline (PBS), 4-(2-hydroxyethyl)-1-piperazineethanesulfonic acid (HEPES), Tris(hydroxymethyl)aminomethane (Tris), 3-(N-morpholino)propanesulfonic acid (MOPS), acetate, water, and a mixture thereof.

In one embodiment, the hydrating solution is PBS.

In further various embodiments, the hydrating solution further comprises a substance to be encapsulated by the inner layer of the bilayer architecture. For example, the substance may be water soluble. In another example, the substance may be lipid soluble. Advantageously, the substance may be released from the composition. Preferably, the substance released from the composition is bioactive or pharmaceutically active.

In the examples to be described in the following paragraphs, the experiments show that a composition comprising a mixture of lipids and copolymers can be made, where the lipids act as an additive that changes the self-assembly and/or aggregation state of the copolymers.

The resulting architectures can be used to encapsulate water-soluble compounds as demonstrated by the encapsulation of calcein. Obviously, they can also be used as carriers for lipophilic compounds.

While the examples show polymer-lipid blends that assemble into tubes, prepared from POPC/PBD-PEG mixtures, and polymer-lipid blends that assemble into vesicles, prepared from biodegradable POPC/PLA-PEG and POPC/PLC-PEG mixtures, it is to be understood and appreciated that the scope of the present disclosure is not limited to such constituents.

In order that the invention may be readily understood and put into practical effect, particular embodiments will now be described by way of the following non-limiting examples.

Examples

Results and Discussion

Spontaneous Tubule Formation in Lipid-Polymer Mixtures

The amphiphilic building blocks used include (1) a block copolymer, $PBD_{22}$-$PEO_{14}$ consisting of a polybutadiene (PBD) hydrophobic block and a poly(ethylene oxide) (PEO) hydrophilic segment ($PBD_{22}$-$PEO_{14}$, MW for the PBD and PEO blocks are 1200 and 600, respectively) and (2) 1-palmitoyl-2-oleoyl-sn-glycero-3-phosphatidylcholine (POPC, MW=760) as the lipid. The lengths of polymer segments produce the ratio of hydrophilic to total mass, $f_{hydrophilic}$=33%, which falls in the range of 29-39%—a general determinant of vesicle-forming capacity of amphiphiles. The hydrophilic PEO segment produces a well-hydrated brush owing to its strong affinity for water and conformational degrees of freedom whereas the hydrophobic PBD segment assembles into a fluid hydrophobic core.

It was recorded the trend in macroscopic optical appearance of the aqueous suspensions consisting of systematically varied molar ratios of $PBD_{22}$-$PEO_{14}$ and POPC using simple optical photography and UV-vis spectroscopy (FIG. 1A-FIG. 1F insets). Treating the optical appearance of the solution as a qualitative indicator for the aggregate morphologies, it was first interpreted the differences in the optical turbidity of the solutions in terms of the morphologies of the amphiphilic aggregates. The suspensions formed, even without extrusion or sonication, from POPC and $PBD_{22}$-$PEO_{14}$ in aqueous solution appear milky, nearly opaque, with a deep "bluish" tinge exhibiting strong absorption at 630 nm, consistent with the expected formation of MLV and large aggregates. In sharp contrast, the mixed composition suspensions display visibly reduced turbidity (FIG. 1, insets) with the equimolar hybrids producing a strikingly transparent suspension and the lowest absorbance at 630 nm—consistent with the spontaneous formation of smaller aggregates or vesicles. This composition-dependent trend in spontaneous vesicle formation in lipid-polymer hybrids suggests the existence of a thermodynamic ground state, which is characterized by small aggregates, rather than the usual large and polydisperse multilamellar vesicles typically obtained for single amphiphiles.

To characterize these amphiphilic mesophases in the aqueous suspensions of mixtures of $PBD_{22}$-$PEO_{14}$ and POPC at different molar ratios, it was carried out electron cryo microscopy (cryoEM) measurements. In addition to providing sub-nanometer scale resolution of morphological features, a key advantage of cryoEM, of direct relevance, is that through flash freezing it allows to image the aggregates in thin vitrified, amorphous ice layers in an unfixed, unstained, and unadsorbed manner, thereby minimizing the damage and deformation typically caused by dehydration, adhesion to support, and osmotic stresses in amphiphilic aggregates. Moreover, the flash-freezing the samples into liquid ethane prevents ice crystal formation and arrests the instantaneous solution structure of the aggregates, providing a good static model of the lipid suspension. Representative cryoEM micrographs, recorded on amorphous ice, for an arbitrary selection of six different compositions (POPC: $PBD_{22}$-$PEO_{14}$, 100:0; 85:15; 75:25; 50:50; 25:75; and 0:100), are shown in FIG. 1.

Figure 1F:
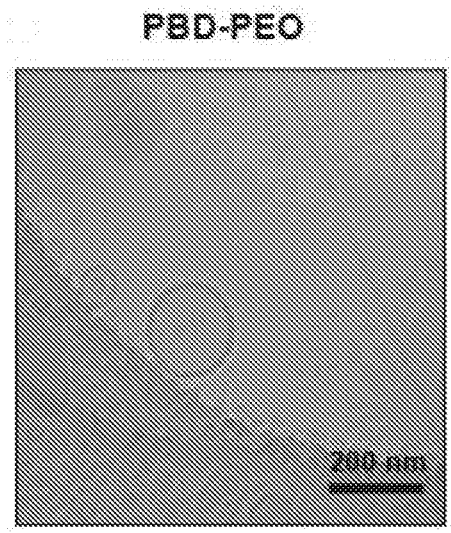
Figure 6A:
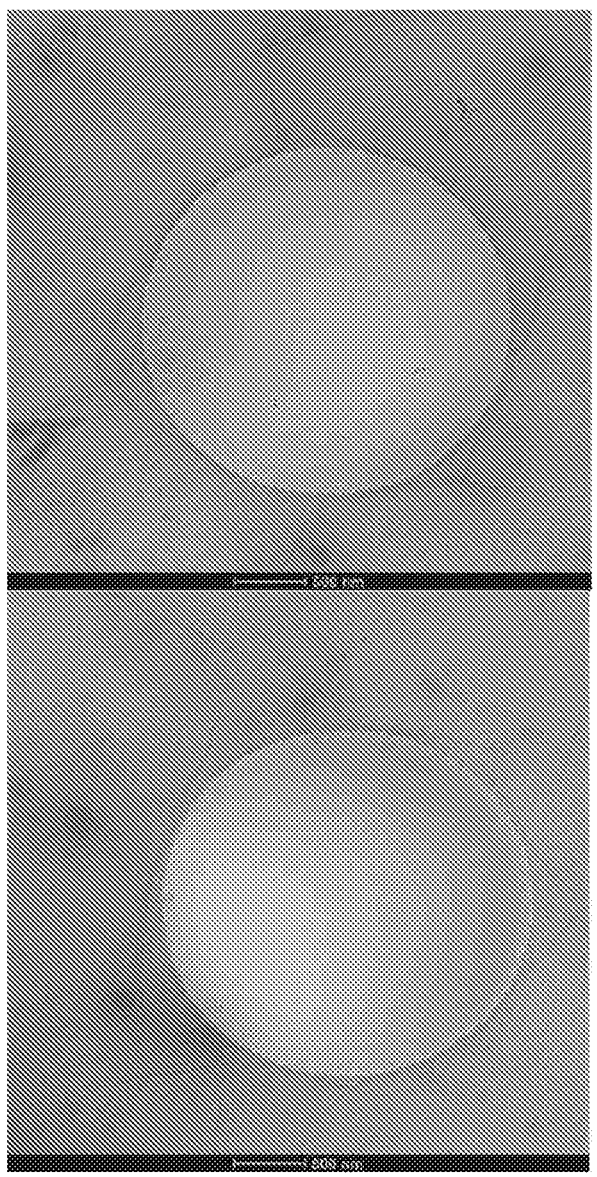
FIG. 6A-6C show the spherical vesicles, among them, are typically between 100-200 nm and the tubules are roughly 20 nm in diameter and extend to hundreds of nanometers, often spanning the entire width of the TEM images in length. 6A. POPC. 6B. POPC/PDB-PEO (50:50). 6C. PDB-PEO.
Figure 6B:
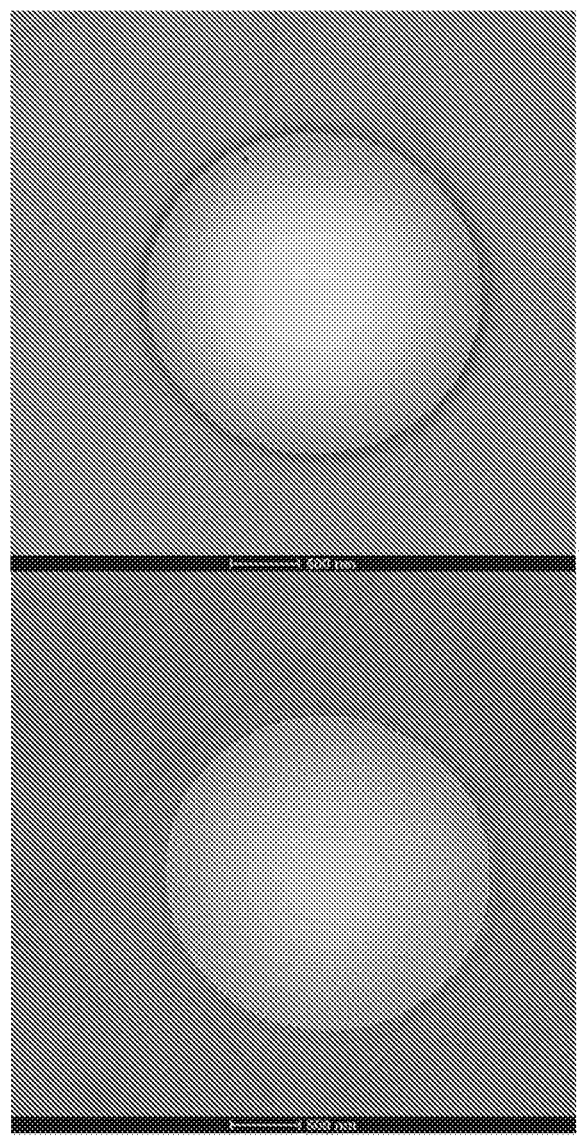
Figure 6C:
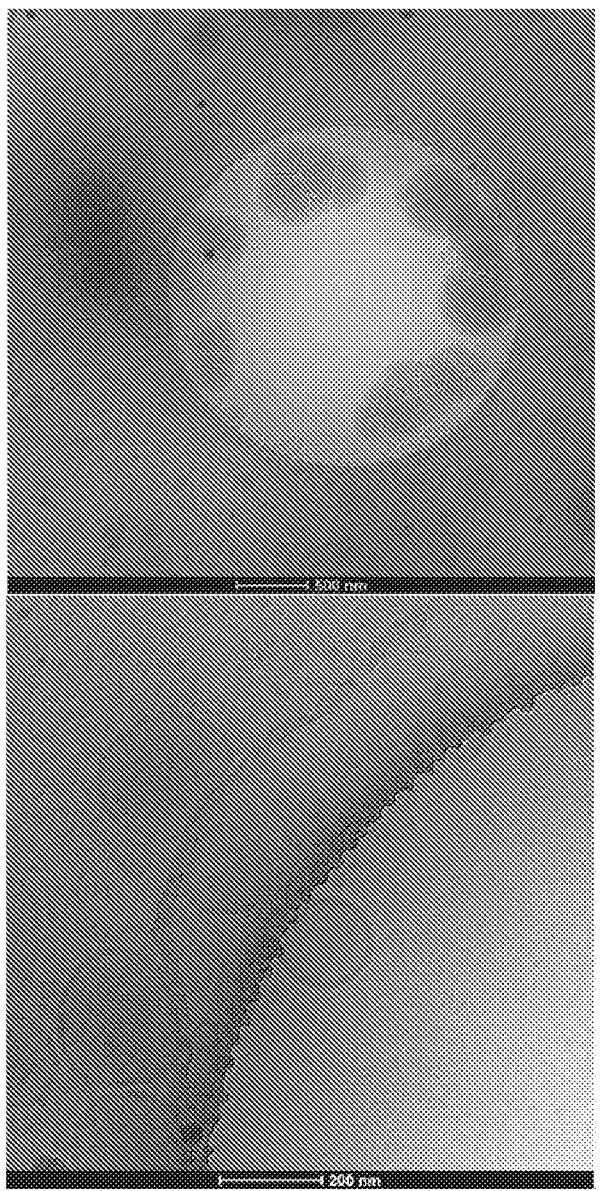

As expected, it is found that each of the two amphiphiles taken alone,—when re-suspended individually in water from dried films above their respective transition temperatures (T>45° C.)—produces aqueous suspensions consisting of highly polydisperse, multilamellar spherical microphases of a variable degree of lamellarity and size (FIG. 1A and FIG. 1F). In contrast, when mixtures of the two amphiphiles, pre-mixed in the dried state, are hydrated by water (or aqueous buffer), they swell to produce mixed mesophases of strikingly different morphologies. Consistent with the optical data, single component $PBD_{22}$-$PEO_{14}$ and POPC on either end of the compositional spectrum reveal heterogeneous mix of large multilamellar vesicles; vesicle-invesicle, vesosomes; and quite rarely deformed vesicles and tubular structures. In contrast, for all mixed, lipid-polymer compositions, a strikingly binary population of mesophase morphologies consisting of co-existing tubular and spherical aggregates is evident (FIG. 1B-1E). The spherical vesicles, among them, are typically between 100-200 nm and the tubules are roughly 20 nm in diameter and extend to hundreds of nanometers, often spanning the entire width of the TEM images in length (FIGS. 6A, 6B, and 6C).

Figure 2A:
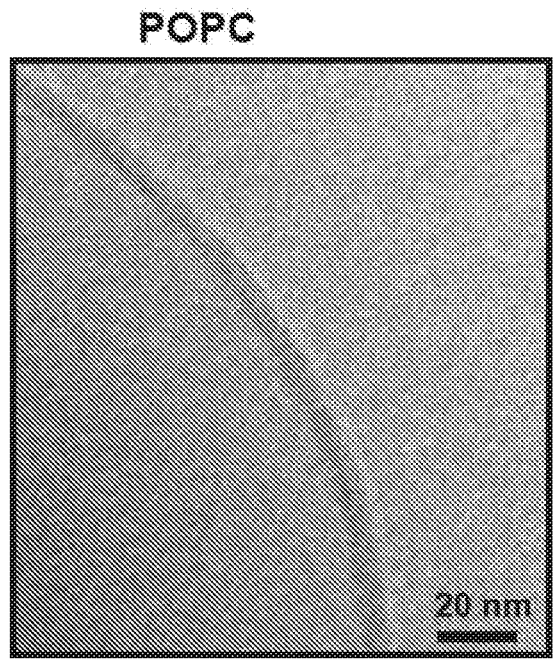
FIG. 2A-2E show wall thickness and density distribution analysis from higher magnification micrographs of vesicles formed by different amphiphiles. 2A. POPC vesicle. 2B. PBD-PEO. 2C, 2D. POPC/PBD-PEO (50:50). Scale bar for 2A, 2B and 2D is 20 nm and 2C is 100 nm. 2E. Line scan plot across the 50:50 tubular membrane, showing the average density distribution and a low density region in the centre of the tube calculated from 17 measurements.
Figure 2B:
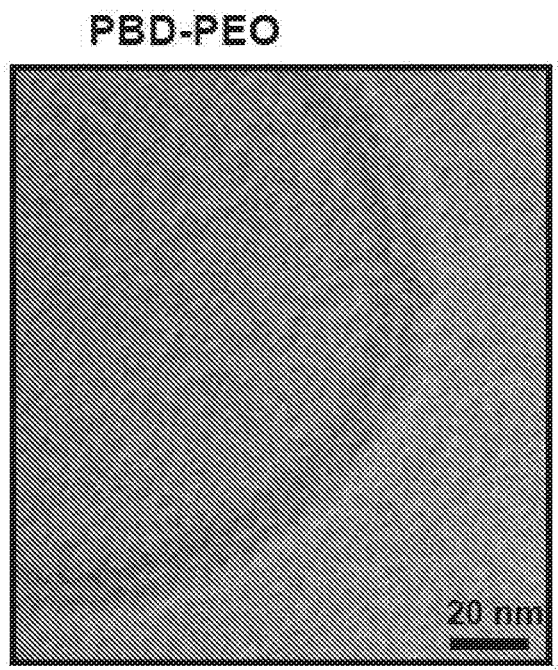
Figure 2C:
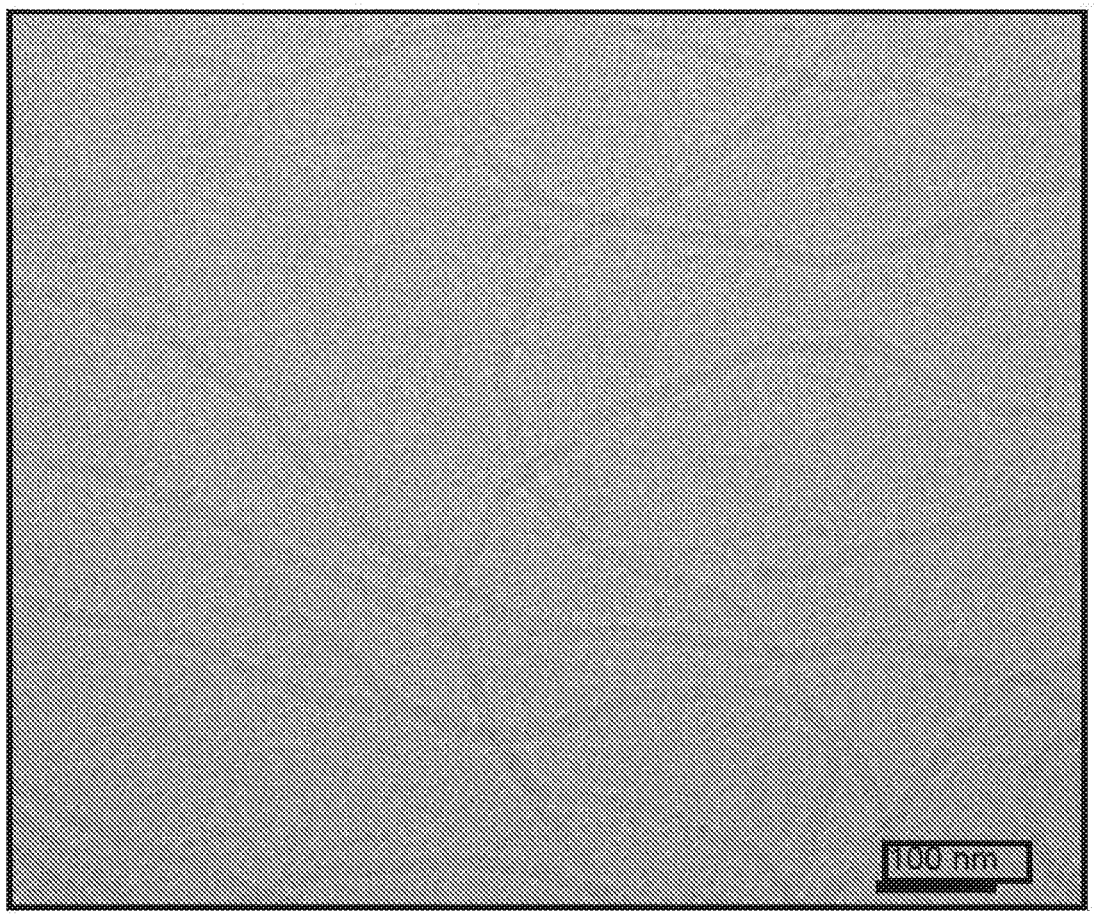
Figure 2D:
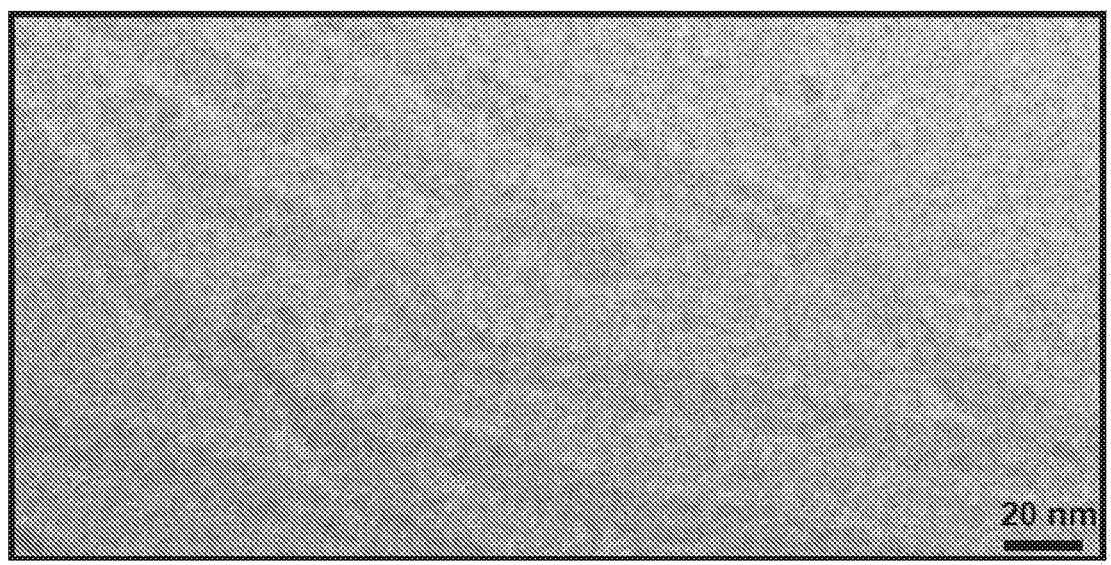

Analysis of cryoEM micrographs of single component mesophases (FIG. 2) reveal that POPC vesicles have a wall thickness of 7.6 nm (SD: 0.9 nm), and the $PBD_{22}$-$PEO_{14}$ with a wall thicknesses of 16.3 nm (SD: 1.5 nm) (FIG. 2A and FIG. 2B). This is in agreement with the formation of shells of single lipid or polymer bilayers. The wall thicknesses, however, do not appear to increase linearly with the proportion of the polymer component, between that of POPC (7.6 nm) and $PBD_{22}$-$PEO_{14}$ (16.3 nm) aggregates, possibly reflecting the complexity of distributions of the two components both laterally and axially across the two leaflets (see below).

Most strikingly, the cryo-EM images reveal that at equimolar composition of POPC and $PBD_{22}$-$PEO_{14}$, the vesicular morphology consists exclusively of membrane tubes with a wall thickness of 14.6 nm (SD: 1.1 nm) (FIGS. 2C and 2D), occasionally displaying elaborate networks with branches and loops, reminiscent of biological membrane tubules and tubulovesicular networks. Note also that, except for gentle mixing, no extraneous mechanical agitation is introduced during preparation of these hybrid mixtures. Although it is difficult to establish that the tubules formed are at true thermodynamic equilibrium, the membrane tubules observed are fully reproducible, independent of sample preparation methods, and remain stable for extended periods of time (>7 days).

Figure 3A:
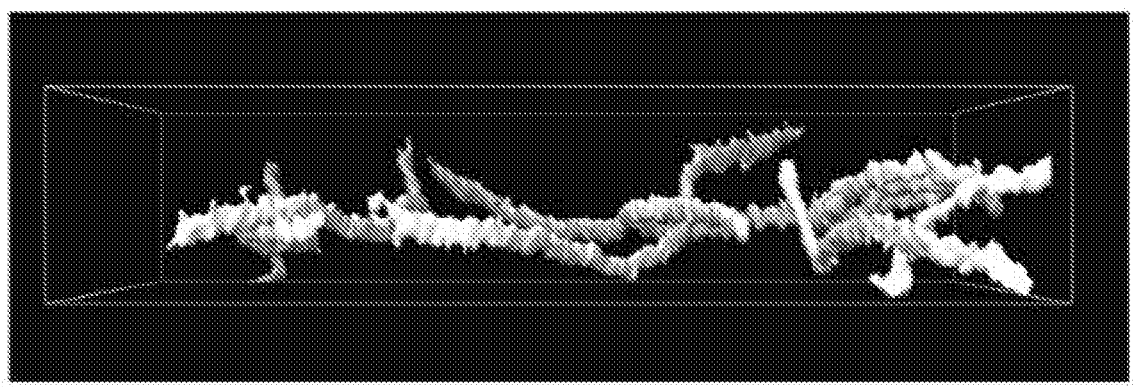
FIG. 3A-3C show cryo electron tomographic analysis of 50:50 POPC-PBD-PEO tubes. 3D surface rendering of a cryo electron tomogram showing the 3D organization of tubes in ice. The three views (3A, 3b, 3C) are related by a 45 degree rotation around the horizontal axis. The white box dimensions are 0.36×1.41×0.93 µm.
Figure 3B:
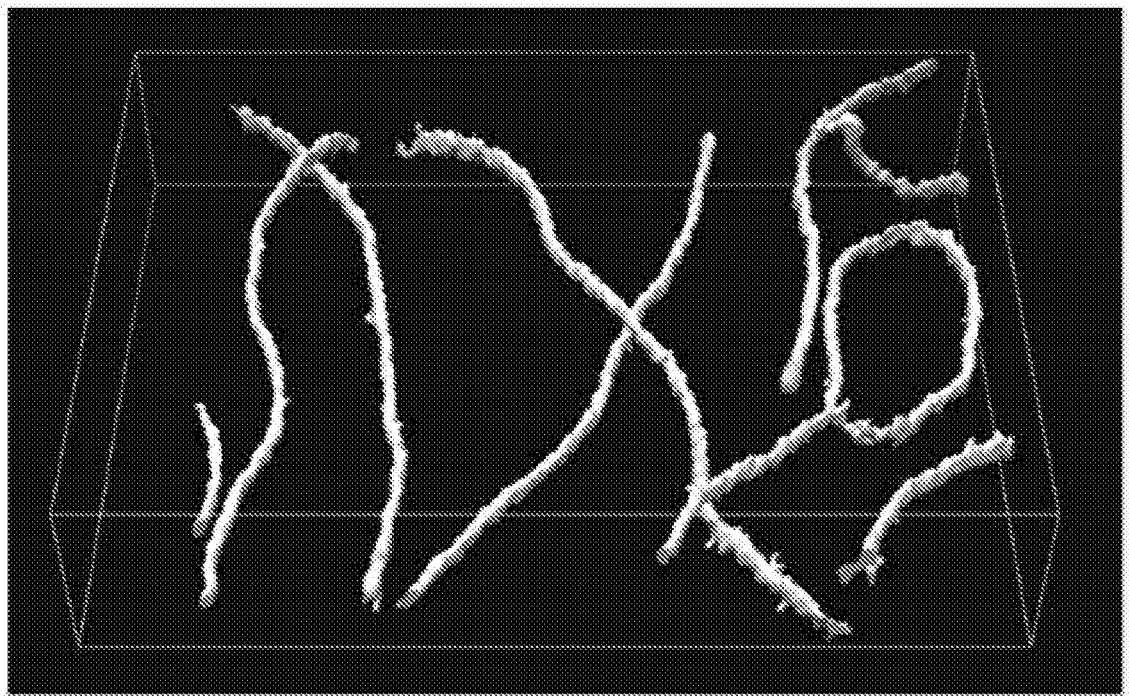
Figure 3C:
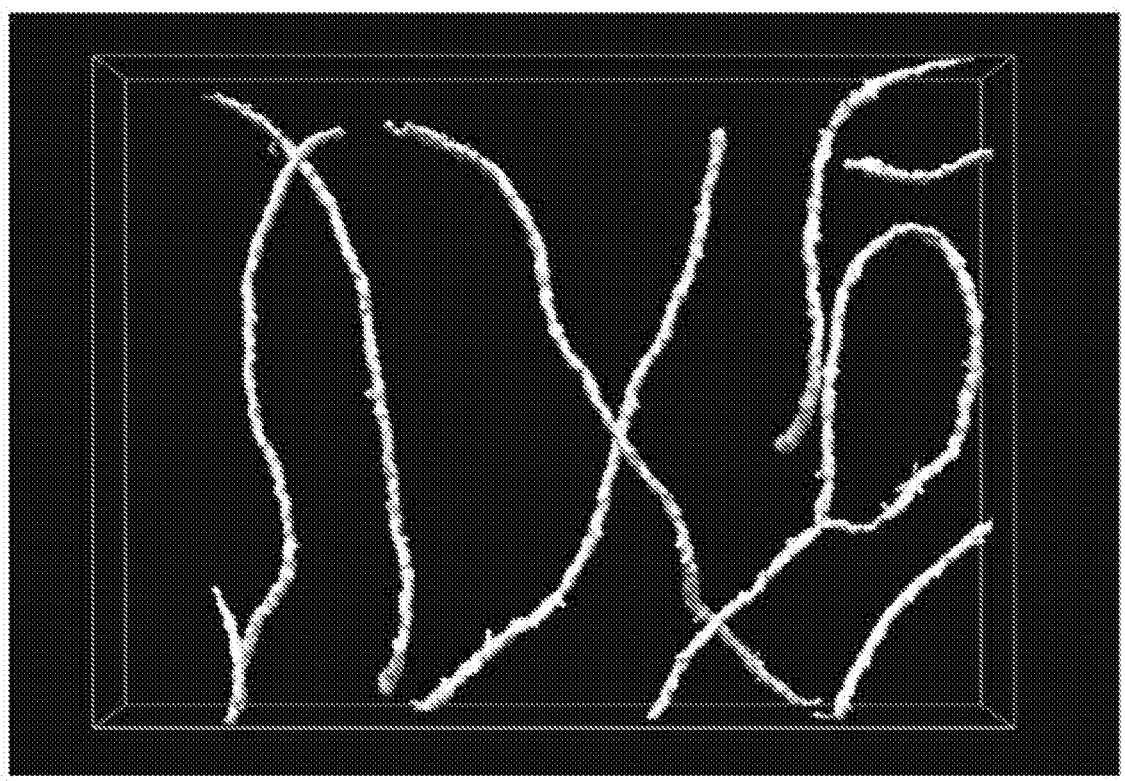
Figure 4A:
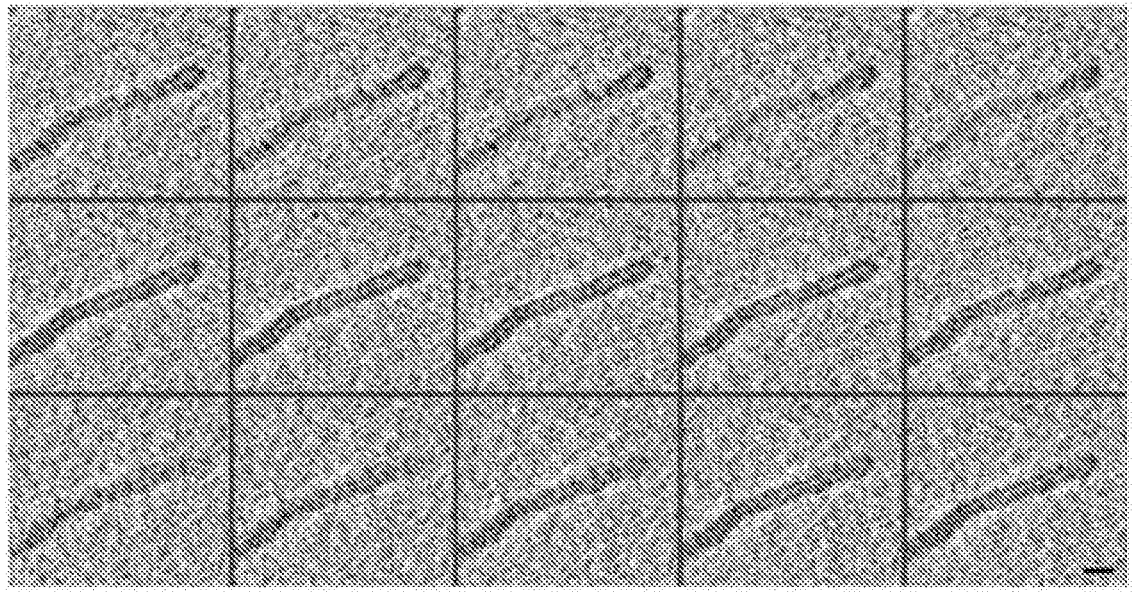
FIG. 4A-4C shows analysis of cross sections through 3D reconstructed tubes revealing a hole in the lumen. Gallery of images showing sequential cross sections of electron tomograms of two membrane tubules. Each image represents a 0.4 nm thick slice through the 3D density. (4A) in a planer orientation and (4B) pointing down in ice. (4C) Line scan plot of the density distribution as shown red (4A). The scale bar is 20 nm.
Figure 4B:
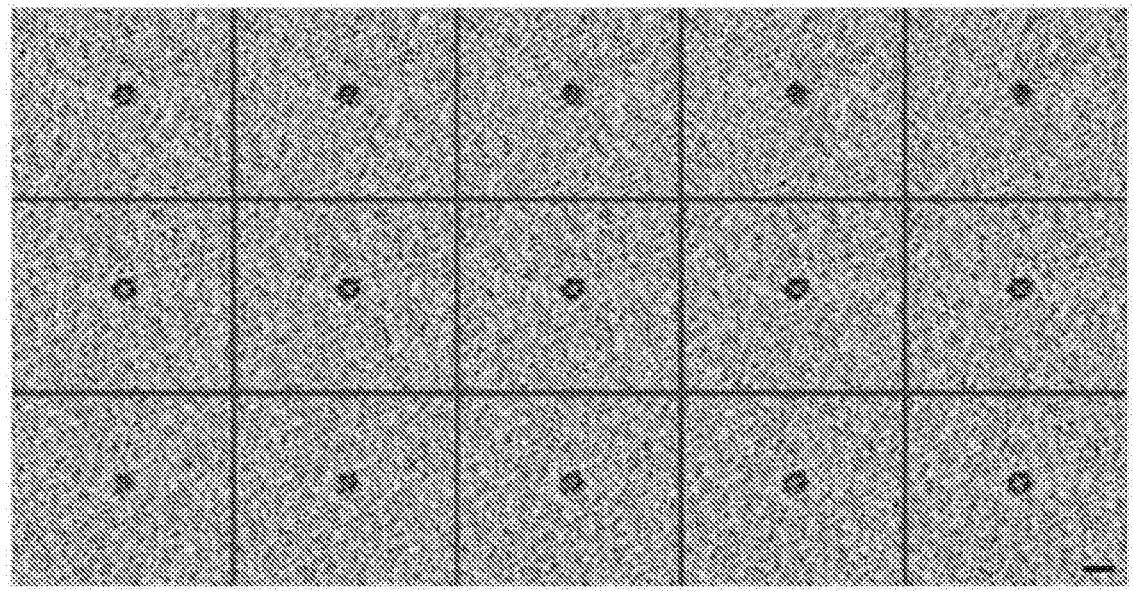
Figure 4C:
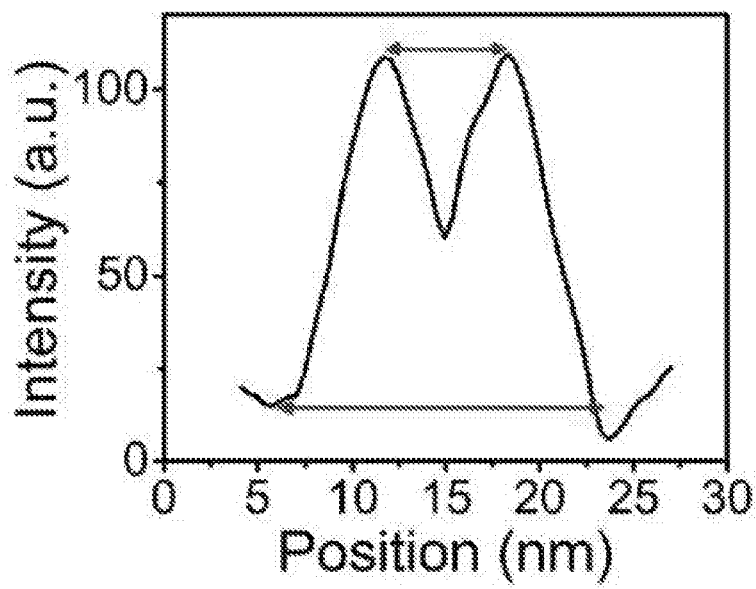

To better characterize the structural attributes of the membrane tubules, including to decipher the nature of the lumen, we calculated the three-dimensional (3D) structure of the tubules formed at the equimolar lipid-polymer composition from cryoEM tilt-series using electron tomography. Specifically, it was reconstructed the cryoEM tilt-series data in 3D by filtered back-projection and refined by simultaneous iterative reconstruction technique (SIRT) (see methods). Moreover, it is also immediately evident that the interior of the tubule invariably displays significantly weaker contrast in comparison to that obtained for the tubule walls. This then indicates that the lumen is characterized by lower electron density, which in turn implies that the lumen is devoid of lipids or polymers of higher electron contrast, consisting primarily of water or the buffer. To elucidate the characteristic details of membrane tubules, a 3D organization was performed by surface rendering and the processed images at 45° around the horizontal axis reveal that there exhibit bends, nodes and loops formation (FIGS. 3A, 3B and 3C). A detailed analysis of tomograms reveals salient features of the lipid polymer tubules. An overview of the 3D organization from surface rendered tomogram reveals that the tubules are randomly dispersed and the processed images at 45° around the horizontal axis reveals that there exhibit conspicuous bends, nodes, and loops forming a prominent tangled tubular network akin to some biological tubulovesicular networks (FIGS. 3A, 3B and 3C). Analyzing geometric properties of several tubules in multiple independent samples indicates that the tubules have an average diameter in a narrow range of 14.6±1.0 nm (n=20). Furthermore, cross-section of electron tomograms of two such lipid polymer tubular structures reveals that it has low density region in the centre of the tubes and high density (darker) regions at the periphery of tubular membranes (FIGS. 4A and 4B). Based on the line-scan analysis (FIG. 4C) of the individual slices for 15 measurements, it is found that the statistically average cross section of the tubular lumen of low electron density contrast (hydrated channel) is 6.5±0.5 nm, establishing that the spontaneously formed aggregates in lipid-polymer mixtures at equimolar composition are indeed vesicular, rather than micellar, structures. The tubules are often longer than the image size with few free ends. A characteristic bulge is clearly seen in the vicinity of the few free-ends. This is not surprising because bulging near the end-caps—where lamellar cylindrical geometry is replaced by a hemi-spherical one—increases the local radius of curvature thus reducing the edge curvature energy. Because formation of lipid nanotubes typically require an external force, the spontaneous appearance of lipid-polymer nanotubes in a strikingly narrow range of diameters suggest that the tubules form as a consequence of mixed self-assembly of lipid and polymer amphiphiles.

To further determine whether the low electron density contrast observed for the lumen of the spontaneously formed, lipid-polymer tubular mesophases in cryoEM experiments indeed reflects the compartmentalized aqueous phase, it was probed whether water-soluble cargo could be stably encapsulated within—(and subsequently released by lysing) the tubules. It was prepared lipid-polymer mesophases with varying molar ratios of the $PBD_{22}$-$PEO_{14}$ polymer (25%, 50%, and 75%) in the presence of self-quenching concentration (50 mM) of a water-soluble fluorescent probe, carboxyfluorescein (CF). After encapsulation, untrapped CF was removed by gel-filtration. Upon lysing the tubules using Triton X-100 (see methods), it is found an increase of fluorescence intensity in excess of two-fold, indicating the CF release and thus the presence of a compartmentalized interior within the tubular mesophases.

Figure 5A:
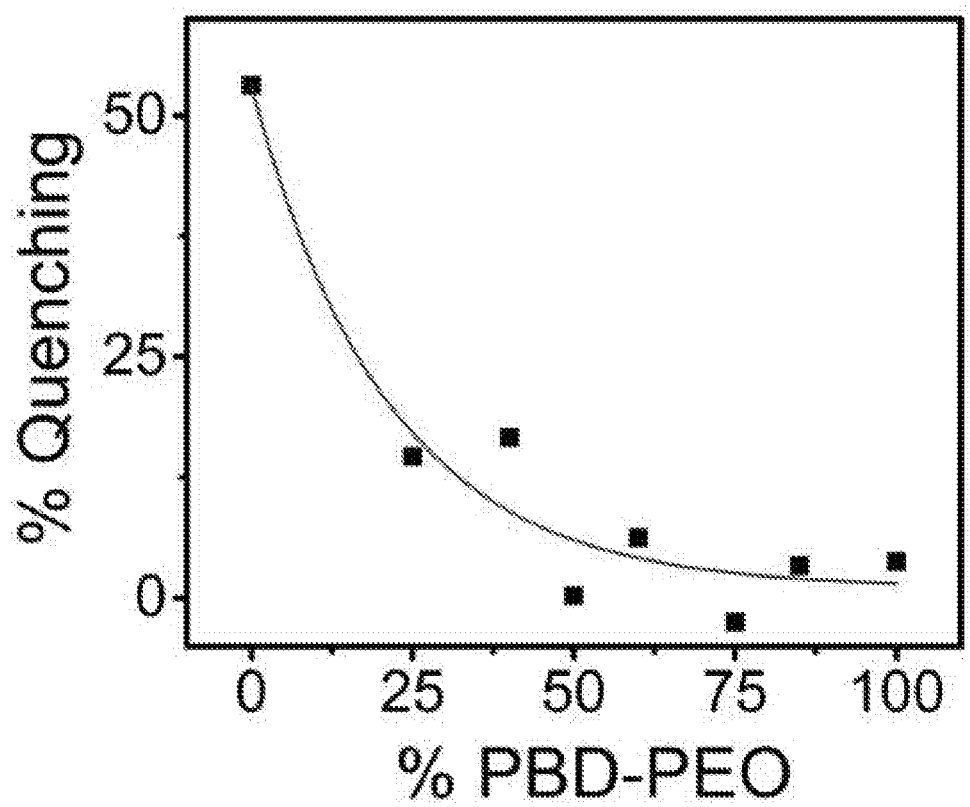
FIG. 5A shows cobalt quenching assay of PBD-PEO/POPC hybrid vesicles at increasing PBD-PEO molar composition. Integrated fluorescence signal from Rhodamine-PE labeled vesicles, before and after 1 mM $CoCl_2$ addition. 10 µL 0.2% Rho-PE labeled vesicle sample was added to 90 µL DI water. $CoCl_2$ was then added to give a final concentration of 1 mM and the decrease in fluorescence was monitored after 1 min at 25° C. Percentage of fluorescence quenching by $CoCl_2$ is calculated using $100\times(F_o-F_{co})/F_o$, where $F_o$ and $F_{co}$ are the measured fluorescence integral area in the absence and in the presence of $Co^{2+}$ quencher, respectively. The theoretical calculated fluorescence quenching for symmetric (lipids and polymers equally distributed) and asymmetric membrane (polymers enriched at outer leaflet) system are indicated.

A requirement for the thermodynamic stabilization of the vesicular state in binary lipid-polymer vesicles is the appearance of a net spontaneous curvature or area-difference between the monolayers, either of which requires asymmetric distribution of the lipid and the polymer components across the two leaflets of the vesicular bilayer. To test whether the relative distribution of the lipid and polymer components in vesicle leaflets is indeed asymmetric, it was carried out a probe-lipid titration assay using metal-ion induced fluorescence quenching. The addition of extra-vesicular divalent cobalt ($Co^{2+}$) ions extinguishes fluorescence from rhodamine-B conjugated lipids (1, 2-dioleoyl-sn-glycero-3-phosphoethanolamine-N-(lissamine rhodamine B sulfonyl) (Rho-PE)) by interacting with the dye. Because $Co^{2+}$ does not diffuse across the lipid bilayer, the extra-vesicular addition only quenches dyes in the exposed outer leaflet. Moreover, rhodamine B conjugated lipids partition preferentially with the lipid phase in lipid-polymer mixtures. Thus, the quenching of rhodamine B provides a reliable indicator, albeit semi-quantitative, of any asymmetry in the distribution of lipid molecules between the two leaflets. The results summarized in FIG. 5A show that for single component POPC vesicles labeled with 0.2 mol % Rho-PE, the theoretical 50% quenching—representing uniform distribution of the dye between the exposed, outer leaflet and shielded, inner one—is achieved. In mixed, POPC/$PBD_{22}$-$PEO_{14}$ vesicle mixtures, on the other hand, the fluorescence quenching by $Co^{2+}$ reveals a noticeable negative departure (decrease in fluorescence quenching to <10%) from this value, reaching a vanishingly low value (<1%) for the equimolar mixture. This then indicates that Rho-PE and hence the lipid component of the vesicle, is depleted from the outer leaflet exposed to the ambient phase lending further support to the notion that lipid and polymer amphiphiles in vesicular mesophases distribute asymmetrically. One reason is that this miscibility gap in molecular distribution between the two leaflets is generated because the large and conformationally labile head-group of the polymer component sterically favours its concentration in the stretched outer leaflet and the lipids of smaller head-groups occupy the compressed inner leaflet. A consequence of this two-dimensional miscibility gap then it produces the conditions for the generation of spontaneous curvature and area difference required for the formation of the tubular vesicles.

Figure 5B:
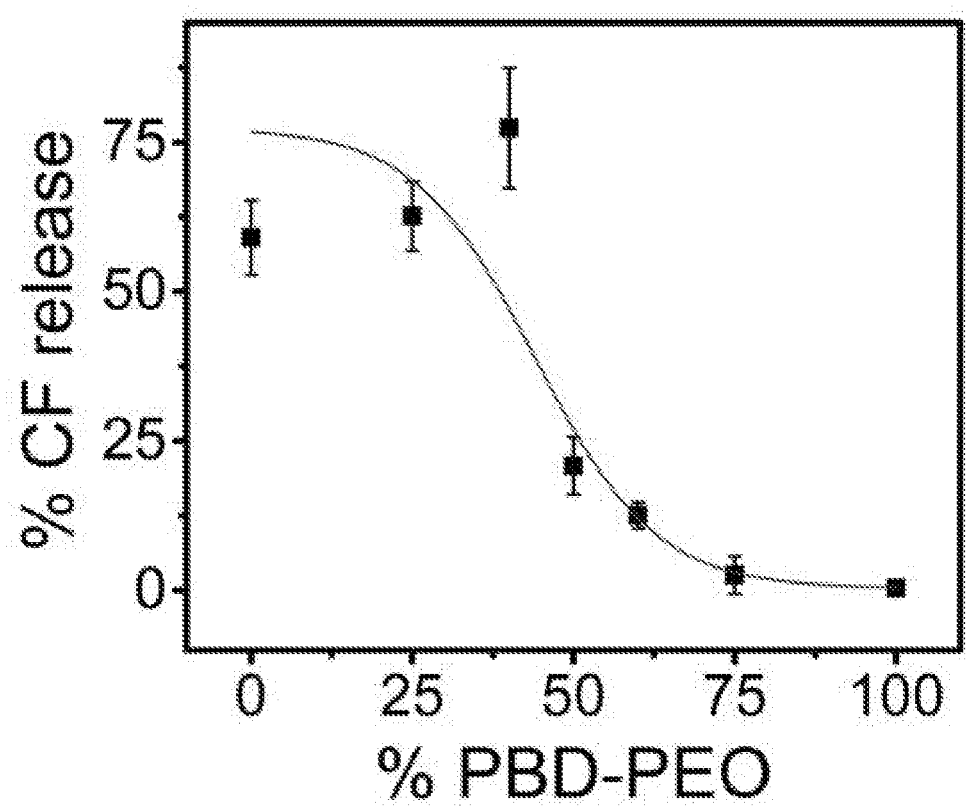
FIG. 5B shows PLA2 activity as quantified by percentage of CF release from vesicles. Percentage CF release ($\lambda_{ex}$=480 nm, $\lambda_{em}$=520 nm) for vesicles of different % mol POPC, after 6000 s incubation with of 150 nM PLA2 and 2 mM $CaCl_2$. The percentage of CF release over time is presented as $100\times(F-F_0)/(F_T-F_0)$, where $F_0$ is the initial fluorescence of CF, F is the fluorescence of CF at time interval t and $F_T$ is the fluorescence intensity after complete release of CF upon adding 0.5% Triton X-100. Data are represented as the mean±standard deviation of two experiments.

A consequence of asymmetric distribution of lipids and polymers in hybrid vesicles is that majority proportion of lipids, which accumulate in the inner leaflet, are shielded from any chemical activity from the exterior. To explore this possibility, it was examined the responsiveness of the hybrid vesicles to a versatile, lipid-hydrolyzing phospholipase, PLA2. PLA2 is a member of the superfamily of interfacially-activated enzymes, which degrades the phospholipid in micellar or vesicular aggregates by cleaving the sn-2 acyl ester bond, producing a free fatty acid and a lysolipid. In experiments, it was used unquenching of apriorily trapped carboxyfluorescein (CF) in POPC/$PBD_{22}$-$PEO_{14}$ as a reporter of loss of vesicle integrity after PLA2 treatment. When PLA2 is incubated with the hybrid POPC/$PBD_{22}$-$PEO_{14}$ vesicles of systematically varied molar ratios, it is found that the PLA2 activity produces a sigmoidal pattern (FIG. 5B). Specifically, it is found that vesicles with <50% mol PBD-PEO reveal greater than 50% PLA2 hydrolysis activity and accompanying CF release. In contrast, vesicles containing high proportions (i.e., 60%, 75% and 100%) of $PBD_{22}$-$PEO_{14}$ exhibit little or no CF release even after 100 min following the PLA2 addition (150 nM). This indicates a rapid diminution of the enzymatic activity at elevated polymer fractions of the POPC/$PBD_{22}$-$PEO_{14}$ hybrid vesicles. The results lend further credence to the foregoing inference that POPC preferably distributes in the inner monolayer of vesicles becoming sterically protected by the outer leaflet $PBD_{22}$-$PEO_{14}$ thus inhibiting the enzymatic action. Because PLA2 is often found at high concentrations in inflammatory cells and pathological tissues of atherosclerosis, pancreatitis, and several forms of cancers, the ability of polymer-lipid hybrid vesicles to resist attack by serum enzymes suggests practical route in producing robust delivery vehicles for drugs and imaging agents, which combine toughness and chemical "inertness" of outer leaflet polymers with the biocompatibility of the inner leaflet lipids, which protect the encapsulated cargo.

Materials and Methods

Materials.

PBD-PEO ($PBD_{22}$-$PEO_{14}$; average molecular weight for the PBD and PEO block: 1200 and 600, respectively) was acquired from Polymer Source. 1-Palmitoyl-2-oleoyl-snglycero-3-phosphatidylcholine (POPC) and 1, 2-dioleoyl-sn-glycero-3-phosphoethanolamine-N-(lissamine rhodamine B sulfonyl) (Rho-PE) were from Avanti Polar Lipids. All other chemicals were purchased from Sigma Aldrich. Deionized (DI) water (18.2 MΩ-cm resistivity) was obtained by purification through a Millipore water purification system.

Preparation of Mixed Lipid-Polymer Membrane Suspensions.

5 mg $mL^{-1}$ stock solutions of PBD-PEO and POPC in chloroform were first mixed in the desired molar ratios: 100:0, 85:15, 75:25, 60:40, 50:50, 40:60, 25:75, 15:85 and 0:100. A 500 μL aliquot of the mixed lipid-polymer stock solution was placed in a 4-mL glass vial and solvent evaporated at 45° C. under a gentle stream of nitrogen. The lipid-polymer cake so obtained was further desiccated for 4 h to obtain a dry, thin lipid film. Vesicles were formed by rehydrating the dried film by adding 1.0 mL of phosphate-buffered saline (PBS, pH 7.4) followed by incubation at 45° C. for 20 minutes, and stirring for 4 hours using a magnetic stirrer at 400 rpm. The vesicle emulsion so achieved has a total amphiphile concentration of 5 mg $ml^{-1}$. To prepare mechanically-extruded vesicles, vesicles sample was repetitively extruded first through polycarbonate membrane of 450 nm pores followed by multiple extrusion cycles (11 or 21 times) through the membranes with 200 nm pores.

Vesicles encapsulating carboxyfluorescein probe were prepared by rehydrating the dried PBD-PEO/POPC films with 1.0 mL of 50 mM CF in 20 mM sodium phosphate, 10 mM NaCl (pH 7.4). Non-encapsulated dye was removed from the emulsion by passing the solution through a gelfiltration PD-10 column (GE Healthcare, Singapore) eluting with 0.1 M PBS buffer, pH=7.4.

Electron Cryo Microscopy and Tomographic Analysis

Figure 2E:
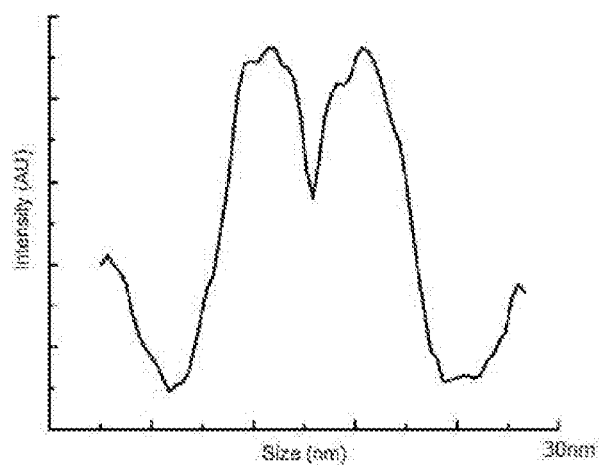

Electron microscope grids, coated with holey carbon film (R2/2 Quantifoil), were glow discharged. 4 μl droplet of sample was deposited onto a grid at 99% humidity, blotted with filter paper, and plunged into liquid ethane (Vitrobot, FEI Company). For tomographic analysis, 10 nm colloidal gold particles in suspension (uncoated EM grade, British Biocell International) was mixed (ratio of 1:3) with the lipid-polymer suspension, before plunge freezing. Cryo grids were imaged using a FEG 200 keV transmission electron microscope (Arctica, FEI Company) equipped with a direct electron detector (Falcon II, Fei Company). Low magnification micrographs in FIG. 1 were recorded at a nominal magnification of 10,500×, giving a final object pixel size of 9.6 Å. Higher magnification images were recorded at 23,000 and 39,500× magnification, corresponding to an object pixel size of 4.2 Å and 2.7 Å respectively. The defocuses used were −20 μm (FIG. 1), −3 μm (FIG. 2), −6 μm (FIG. 3-4). Single axis tilt series were collected ±60 degrees, recording images at two degree increment. Automatic low dose data acquisition routines were used to minimize radiation damage. The total dose per tilt series was 61 electrons/Å2. The tilt series were aligned using 10 nm colloidal gold particles as fiducial markers, and reconstructed in 3D by filtered backprojection and SIRT (IMOD software package). 3D reconstructions were visualized in 3dmod, and Chimera. Wall thickness measurements were carried out 20 times for each sample. Line scans to plot density distribution were carried out in ImageJ. The plot in FIG. 2E is an average of 17 line scans, using a line width of 50 pixels (21 nm). Three out of twenty measurements were excluded from the average, as these regions did not display a low-density region in the centre. For representing the objects more clearly, 3D organization of the tubular membranes were shown by surface rendering (FIG. 3), the tomograms were processed in Chimera using a 3×3 median filter and a remove-noise option. The raw tomographic data (without additional post processing) is presented in FIG. 4.

Turbidity Measurements Using UV-Vis Spectrophotometer

Turbidity data were collected using Perkin-Elmer UV-visible Spectrophotometer (Lambda 35) equipped with a low volume quartz cuvette of 1.0 cm path length. Absorbance was measured by loading the cuvette with 100 μL vesicle suspension over the spectral range spanning 800 to 550 nm in 2 nm steps. Results (absorbance at 630 nm) are presented as a function of PBD-PEO molar fraction for the pre-extruded and extruded 5 mg $mL^{-1}$ PBD-PEO/POPC hybrid vesicle emulsions. 630 nm was chosen because at this wavelength the polymer has minimal absorption, and any attenuation of light comes from scattering of the aggregates.

Membrane Asymmetry Characterization Using Fluorescence Quenching Assay

A 10 μL aliquot of an extruded 0.2% Rho-PE labeled vesicle solution was diluted by adding 90 μL DI water in a cuvette. $CoCl_2$ was then added to the cuvette from a 10 mM stock solution, to achieve a final concentration of 0.2-1.0 mM and the change in fluorescence signal was recorded at 25° C. 1 min after the addition of $Co^{2+}$. The fluorescence intensity was measured at 500-650 nm (band slit=5 nm) with excitation at 470 nm (band slit=5 nm) using a Fluoro log 3 total fluorescence, i.e., after full release of CF upon addition of 0.5% Triton X-100. The experiment was repeated twice.

Table 1 shows the various blends and controls prepared according to the procedures detailed above. As controls, PBD-PEG, PBD-PEG/POPC, and POPC-based formulations were prepared as well.

TABLE 1

| Sample ID | Polymer | Lipid | Details |
|---|---|---|---|
| 0.7 | Polyethylene glycol-block-polycaprolactone {PEG-PCL 550-b-700} | None | |
| 0.7_POPC | Polyethylene glycol-block-polycaprolactone {PEG-PCL 550-b-700} | 1-palmitoyl-2-plepyl-sn-glycero-3-phosphocholine (POPC) | 1 to 1 molar blend |
| 1.1 | Polyethylene glycol-block-polycaprolactone {PEG-PCL 550-b-1100} | | |
| 1.1_POPC | Polyethylene glycol-block-polycaprolactone {PEG-PCL 550-b-1100} | 1-palmitoyl-2-oleoyl-sn-glycero-3-phosphocholine (POPC) | 1 to 1 molar blend |
| 2.6 | Polyethylene glycol-block-polycaprolactone {PEG-PCL 2000-b-2600} | | |
| 2.6_POPC | Polyethylene glycol-block-polycaprolactone {PEG-PCL 2000-b-2600} | 1-palmitoyl-2-oleoyl-sn-glycero-3-phosphocholine (POPC) | 1 to 1 molar blend |
| PEG-PLA_1.9 | Polyethylene glycol-block-polylactic acid (PEG-PLA 700-b-1900) | | |
| PEG-PLA_1.9_POPC | Polyethylene glycol-block-polylactic acid (PEG-PLA 550-b-1900) | 1-palmitoyl-2-oleoyl-sn-glycero-3-phosphocholine (POPC) | 1 to 1 molar blend |
| PEG-PLA_2.75 | Polyethylene glycol-block-polylactic acid (PEG-PLA 550-b-2750) | | |
| PEG-PLA_2.75_POPC | Polyethylene glycol-block-polylactic acid (PEG-PLA 550-b-2750) | 1-palmitoyl-2-oleoyl-sn-glycero-3-phosphocholine (POPC) | 1 to 1 molar blend | fluorometer (Horiba Jobin Yvon Inc., Edison N.J.). Percentage fluorescence quenching (% quenching) was calculated as: $100\times(F_o-F_{co})/F_o$, where $F_o$ and $F_{co}$ represent the measured fluorescence intensity in the absence and the presence of $Co^{2+}$ quencher, respectively. For vesicles impermeable to $Co^{2+}$ quencher, % quenching represents the fraction of the Rho-PE fluorescent probe in the outer leaflets of the vesicles. For unilamellar vesicles with Rho-PE distributed equally between the inner and outer membrane leaflet, % quenching theoretically equals 50. Percentage quenching below 50 or above 50 then represent deviation in Rho-PE distribution across the two leaflets, providing a measure of asymmetry in lipid distribution.

Phospholipase A2 Assay

For phospholipase A2 (PLA2) assay, 1.0 mL of 50 mM carboxyfluorescein (CF; self-quenching concentration) dissolved in HEPES CF buffer (100 mM KCl, 10 mM HEPES (2-[4-(2-hydroxyethyl)piperazin-1-yl]ethanesulfonic acid), pH 7.4) was added to the dried PBD-PEO/POPC films, after which vesicle suspension was prepared and extruded as described above. Non-entrapped CF was removed via gel filtration using a PD-10 column (GE Healthcare, Singapore) eluting with HEPES KCl-adjusted buffer (150 mM KCl, 10 mM HEPES, pH 7.4). When CF is released from the vesicles in the surrounding aqueous buffer, fluorescence intensity increases because of dequenching.

Gel-filtered CF-encapsulating vesicles (5 μL) were mixed with 195 μL HEPES KCl-adjusted buffer in a 96 well-plate with 2 mM $CaCl_2$. The release of CF from the vesicles, as result of the addition of 150 nM PLA2 from honey bee venom (Apis mellifera) monitored as a function of time at room temperature using a fluorescence plate reader (Infinite 200, Tecan, Salzburg, Austria; λex=480 nm, λem=520 nm). The time between gel filtration of the vesicles and the start of the PLA2 assay experiment was kept within 30 min. The percentage of CF release over time is presented by $100\times(F-F_0)/(F_T-F_0)$, where $F_0$ is the initial fluorescence of CF, F is the fluorescence of CF at time interval t and $F_T$ represents The formation of aqueous compartments/vesicular structures/tubular structures was initially assessed by encapsulation of a water-soluble fluorescent dye (calcein) at self-quenching concentrations (ca 30 mM). Enscapsulation was assessed by measuring the fluorescence before (control) and after disruption of the self-assembled structures by a membrane-dissolving dye (tx-100).

Figure 7A:
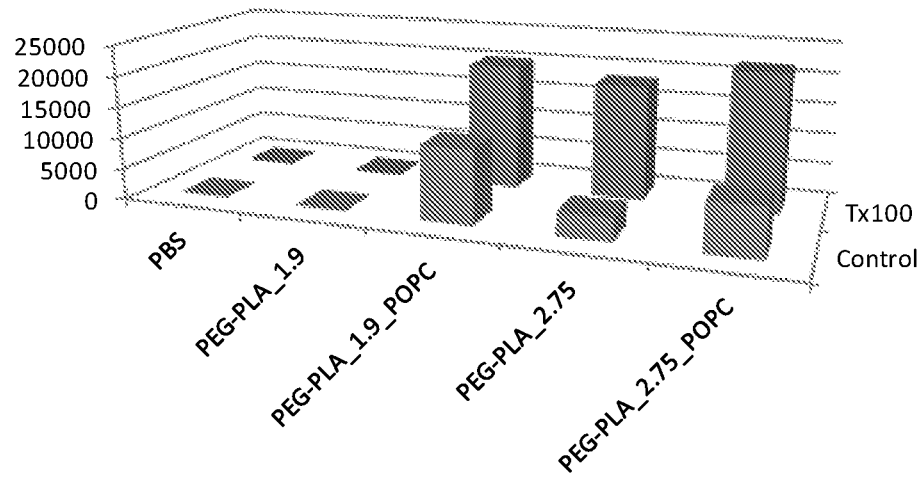
FIG. 7A-C shows fluorescence intensity before and after addition of tx-100 for PEG-PLA blends (7A), PEG-PBD blends (7B), PEG-PCL blends (7C). For all polymers it was observed that no encapsulation occurred when the polymers alone were employed. However, in combination with a lipid (POPC), structures were formed that were able to encapsulate fluorescent dyes, indicating that membrane enclosed architectures were formed.
Figure 7B:
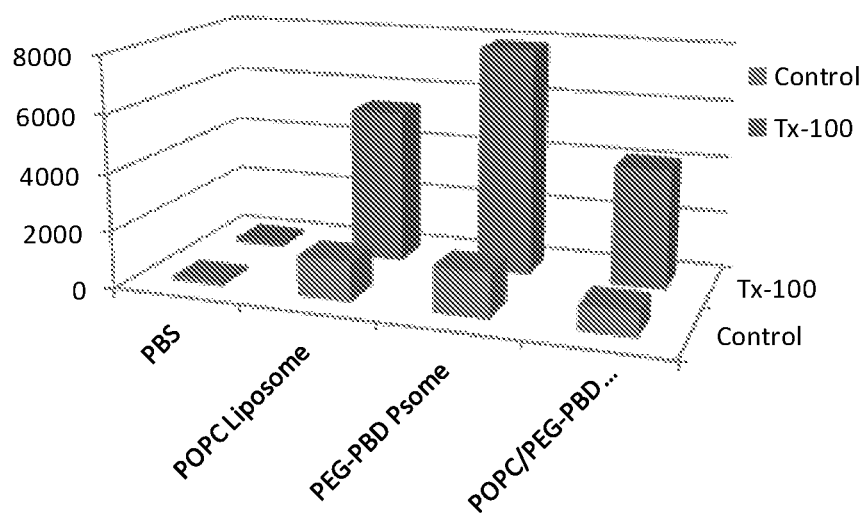
Figure 7C:
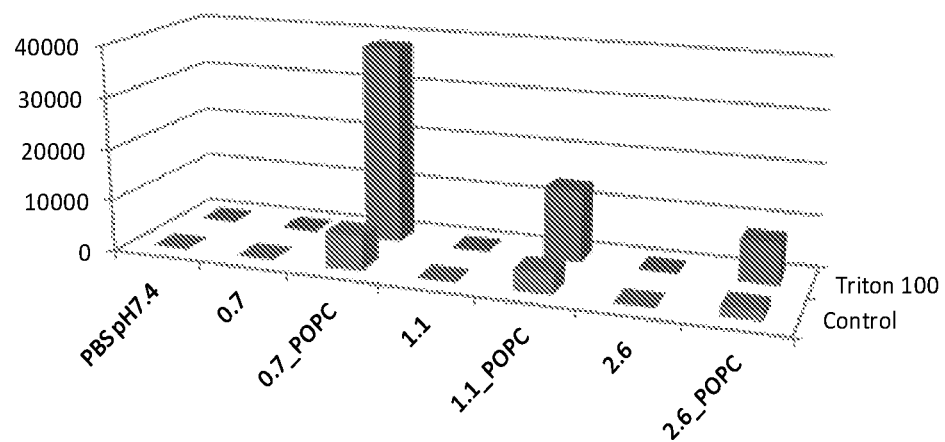

FIG. 7A-C shows fluorescence intensity before and after addition of tx-100 for PEG-PLA blends (7A), PEG-PBD blends (7B), PEG-PCL blends (7C). For all polymers it was observed that no encapsulation occurred when the polymers alone were employed. However, in combination with a lipid (POPC), structures were formed that were able to encapsulate fluorescent dyes, indicating that membrane enclosed architectures were formed.

Figure 8:
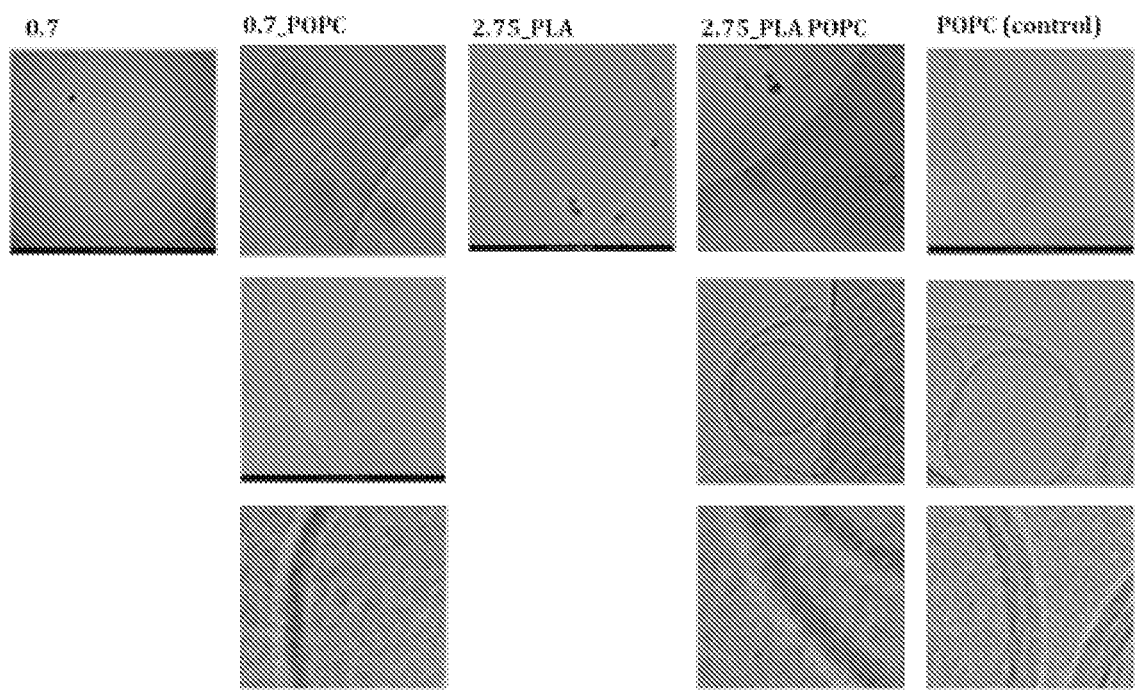
FIG. 8 shows representative Cryo-TEM images for 5 samples subjected to Cryo-TEM (electron microscopy) analysis and DLS (data not shown). In agreement with the dye leakage studies, vesicular structures were observed for those formulations that exhibited encapsulation (i.e., lipids alone or lipid polymer blends), whereas no such structures where observed for the formulations that did not show encapsulation (i.e., polymers alone).

To investigate the structures formed, 5 samples were subjected to Cryo-TEM (electron microscopy) analysis and DLS (data not shown) (FIG. 8). In agreement with the dye leakage studies, vesicular structures were observed for those formulations that exhibited encapsulation (i.e., lipids alone or lipid polymer blends), whereas no such structures where observed for the formulations that did not show encapsulation (i.e., polymers alone).

The polymer blends displayed a membrane ultrastructure with a clear singular electron dense inner layer embedded within two layers of much reduced electron densiry. POPC on the other hand exhibited a somewhat less pronounced electrondense layer, which, upon closer inspection, revealed the existence of two lamellea separated by an ultrathin inner layer of lower electron density. The POPC membrane also appeared undulated (wavy), as compared to the polymer lipid blend, which appeared to show a more rigid membrane. The organization of the lipid membrane is in accordance with literature observations.

Figure 9:
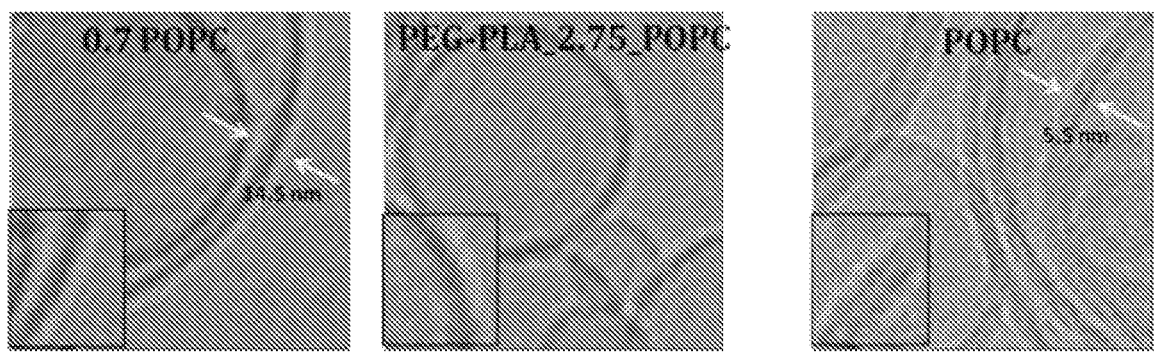
FIG. 9 shows membrane thicknesses of the various polymer blend were 14.5 nm if all three layers were taken into account, and 6.5 nm when only the electron-dense layer was taken. The POPC membranes showed a thickness of 5.5 nm. Overall, this indicated that the vesicles formed from lipid-polymer mixtures were composed of polymers and lipid, since they were observably different form POPC membranes, and without lipid present, membranes would not form.

FIG. 9 shows membrane thicknesses of the various polymer blend were 14.5 nm if all three layers were taken into account, and 6.5 nm when only the electron-dense layer was taken. The POPC membranes showed a thickness of 5.5 nm. Overall, this indicated that the vesicles formed from lipid-polymer mixtures were composed of polymers and lipid, since they were observably different form POPC membranes, and without lipid present, membranes would not form.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

REFERENCES

1. Dabora, S. L. and M. P. Sheetz (1988). "THE MICROTUBULE-DEPENDENT FORMATION OF A TUBULO-VESICULAR NETWORK WITH CHARACTERISTICS OF THE ER FROM CULTURED-CELL EXTRACTS." Cell 54(1): 27-35.
2. Discher, B. M., Y. Y. Won, D. S. Ege, J. C. M. Lee, F. S. Bates, D. E. Discher and D. A. Hammer (1999). "Polymersomes: Tough vesicles made from diblock copolymers." Science 284(5417): 1143-1146.
3. Geng, Y., Dalhaimer, P., Cai, S., Tsai, R., Tewari, M., Minko, T., Discher, D. E. Shape effects of filaments versus spherical particles in flow and drug delivery (2007) Nature Nanotechnology, 2 (4), pp. 249-255.
4. McMahon, H. T. and J. L. Gallop (2005). "Membrane curvature and mechanisms of dynamic cell membrane remodelling." Nature 438(7068): 590-596.
5. Roux, A., G. Cappello, J. Cartaud, J. Prost, B. Goud and P. Bassereau (2002). "A minimal system allowing tubulation with molecular motors pulling on giant liposomes." Proceedings of the National Academy of Sciences of the United States of America 99(8): 5394-5399.
6. Stachowiak, J. C., F. M. Brodsky and E. A. Miller (2013). "A cost-benefit analysis of the physical mechanisms of membrane curvature." Nature Cell Biology 15(9): 1019-1027.
7. Zimmerberg, J. and M. M. Kozlov (2006). "How proteins produce cellular membrane curvature." Nature Reviews Molecular Cell Biology 7(1): 9-19.
8. Adrian, M., J. Dubochet, J. Lepault and A. W. McDowall (1984). "CRYO-ELECTRON MICROSCOPY OF VIRUSES." Nature 308(5954): 32-36.
9. Ajo-Franklin, C. M., C. Yoshina-Ishii and S. G. Boxer (2005). "Probing the structure of supported membranes and tethered oligonucleotides by fluorescence interference contrast microscopy." Langmuir 21(11): 4976-4983.
10. Bangham, A. D. and R. W. Horne (1964). "NEGATIVE STAINING OF PHOSPHOLIPIDS+THEIR STRUCTURAL MODIFICATION BY-SURFACE ACTIVE AGENTS AS OBSERVED IN ELECTRON MICROSCOPE." Journal of Molecular Biology 8(5): 660-&.
11. Canham, P. B. (1970). "MINIMUM ENERGY OF BENDING AS A POSSIBLE EXPLANATION OF BICONCAVE SHAPE OF HUMAN RED BLOOD CELL." Journal of Theoretical Biology 26(1): 61-&.
12. Dabora, S. L. and M. P. Sheetz (1988). "THE MICROTUBULE-DEPENDENT FORMATION OF A TUBULO-VESICULAR NETWORK WITH CHARACTERISTICS OF THE ER FROM CULTURED-CELL EXTRACTS." Cell 54(1): 27-35.
13. Degennes, P. G. (1980). "CONFORMATIONS OF POLYMERS ATTACHED TO AN INTERFACE." Macromolecules 13(5): 1069-1075.
14. Dennis, E. A., J. Cao, Y.-H. Hsu, V. Magrioti and G. Kokotos (2011). "Phospholipase A2 Enzymes: Physical Structure, Biological Function, Disease Implication, Chemical Inhibition, and Therapeutic Intervention." Chemical Reviews 111(10): 6130-6185.
15. Discher, B. M., Y. Y. Won, D. S. Ege, J. C. M. Lee, F. S. Bates, D. E. Discher and D. A. Hammer (1999). "Polymersomes: Tough vesicles made from diblock copolymers." Science 284(5417): 1143-1146.
16. Discher, D. E. and F. Ahmed (2006). Polymersomes. Annual Review of Biomedical Engineering. Palo Alto, Annual Reviews. 8: 323-341.
17. Discher, D. E. and A. Eisenberg (2002). "Polymer vesicles." Science 297(5583): 967-973.
18. Griffiths, G. and K. Simons (1986). "THE TRANS GOLGI NETWORK—SORTING AT THE EXIT SITE OF THE GOLGI-COMPLEX." Science 234(4775): 438-443.
19. Helfrich, W. (1973). "ELASTIC PROPERTIES OF LIPID BILAYERS—THEORY AND POSSIBLE EXPERIMENTS." Zeitschrift Fur Naturforschung C-a Journal of Biosciences C28(11-1): 693-703.
20. Koster, A. J., R. Grimm, D. Typke, R. Hegerl, A. Stoschek, J. Walz and W. Baumeister (1997). "Perspectives of molecular and cellular electron tomography." Journal of Structural Biology 120(3): 276-308.

21. Kremer, J. R., D. N. Mastronarde and J. R. McIntosh (1996). "Computer Visualization of Three-Dimensional Image Data Using IMOD." Journal of Structural Biology 116(1): 71-76.
22. Kugiyama, K., Y. Ota, K. Takazoe, Y. Moriyama, H. Kawano, Y. Miyao, T. Sakamoto, H. Soejima, H. Ogawa, H. Doi, S. Sugiyama and H. Yasue (1999). "Circulating Levels of Secretory Type II Phospholipase A2 Predict Coronary Events in Patients with Coronary Artery Disease." Circulation 100(12): 1280-1284.
23. Lee, C. and L. B. Chen (1988). "DYNAMIC BEHAVIOR OF ENDOPLASMIC-RETICULUM IN LIVING CELLS." Cell 54(1): 37-46.
24. Lin, W.-C., C. D. Blanchette, T. V. Ratto and M. L. Longo (2006). "Lipid Asymmetry in DLPC/DSPC-Supported Lipid Bilayers: A Combined AFM and Fluorescence Microscopy Study." Biophysical Journal 90(1): 228-237.
25. Lucic, V., F. Forster and W. Baumeister (2005). Structural studies by electron tomography: From cells to molecules. Annual Review of Biochemistry. Palo Alto, Annual Reviews. 74: 833-865.
26. Marques, E. F. (2000). "Size and Stability of Catanionic Vesicles: Effects of Formation Path, Sonication, and Aging." Langmuir 16(11): 4798-4807.
27. Maxfield, F. R. and T. E. McGraw (2004). "Endocytic recycling." Nature Reviews Molecular Cell Biology 5(2): 121-132.
28. McMahon, H. T. and J. L. Gallop (2005). "Membrane curvature and mechanisms of dynamic cell membrane remodelling." Nature 438(7068): 590-596.
29. Miao, L., U. Seifert, M. Wortis and H. G. Dobereiner (1994). "BUDDING TRANSITIONS OF FLUID-BILAYER VESICLES—THE EFFECT OF AREA-DIFFERENCE ELASTICITY." Physical Review E 49(6): 5389-5407.
30. Murakami, M., Y. Taketomi, H. Sato and K. Yamamoto (2011). "Secreted phospholipase A2 revisited." Journal of Biochemistry 150(3): 233-255.
31. Nevalainen, T. J. (1993). "Serum phospholipases A2 in inflammatory diseases." Clinical Chemistry 39(12): 2453-2459.
32. Pettersen, E. F., T. D. Goddard, C. C. Huang, G. S. Couch, D. M. Greenblatt, E. C. Meng and T. E. Ferrin (2004). "UCSF Chimera—A visualization system for exploratory research and analysis." Journal of Computational Chemistry 25(13): 1605-1612.
33. Presley, J. F., N. B. Cole, T. A. Schroer, K. Hirschberg, K. J. M. Zaal and J. LippincottSchwartz (1997). "ER-to-Golgi transport visualized in living cells." Nature 389 (6646): 81-85.
34. Ramirez, F. and M. K. Jain (1991). "PHOSPHOLIPASE-A2 AT THE BILAYER INTERFACE." Proteins-Structure Function and Genetics 9(4): 229-239.
35. Rodriguez-Garcia, R., M. Mell, I. Lopez-Montero, J. Netzel, T. Hellweg and F. Monroy (2011). "Polymersomes: smart vesicles of tunable rigidity and permeability." Soft Matter 7(4): 1532-1542.
36. Roux, A., G. Cappello, J. Cartaud, J. Prost, B. Goud and P. Bassereau (2002). "A minimal system allowing tubulation with molecular motors pulling on giant liposomes." Proceedings of the National Academy of Sciences of the United States of America 99(8): 5394-5399.
37. Safran, S. A., P. Pincus and D. Andelman (1990). "THEORY OF SPONTANEOUS VESICLE FORMATION IN SURFACTANT MIXTURES." Science 248 (4953): 354-356.
38. Scaglione, B. A. and D. A. Rintoul (1989). "A fluorescence-quenching assay for measuring permeability of reconstituted lens MIP26." Investigative Ophthalmology & Visual Science 30(5):961-966.
39. Schneider, C. A., W. S. Rasband and K. W. Eliceiri (2012). "NIH Image to ImageJ: 25 years of image analysis." Nat Meth 9(7): 671-675.
40. Sheetz, M. P. and S. J. Singer (1974). "BIOLOGICAL-MEMBRANES AS BILAYER COUPLES—MOLECULAR MECHANISM OF DRUG-ERYTHROCYTE INTERACTIONS." Proceedings of the National Academy of Sciences of the United States of America 71(11): 4457-4461.
41. Stachowiak, J. C., F. M. Brodsky and E. A. Miller (2013). "A cost-benefit analysis of the physical mechanisms of membrane curvature." Nature Cell Biology 15(9): 1019-1027.
42. Svetina, S., M. Brumen and B. Zeks (1985). "LIPID BILAYER ELASTICITY AND THE BILAYER COUPLE INTERPRETATION OF RED-CELL SHAPE TRANSFORMATIONS AND LYSIS." Studia Biophysica 110(1-3): 177-184.
43. Trucco, A., R. S. Polishchuk, O. Martella, A. Di Pentima, A. Fusella, D. Di Giandomenico, E. San Pietro, G. V. Beznoussenko, E. V. Polishchuk, M. Baldassarre, R. Buccione, W. J. C. Geerts, A. J. Koster, K. N. J. Burger, A. A. Mironov and A. Luini (2004). "Secretory traffic triggers the formation of tubular continuities across Golgi subcompartments." Nature Cell Biology 6(11):1071-U1011.
44. Weidman, P., R. Roth and J. Heuser (1993). "GOLGI MEMBRANE DYNAMICS IMAGED BY FREEZE-ETCH ELECTRON-MICROSCOPY—VIEWS OF DIFFERENT MEMBRANE COATINGS INVOLVED IN TUBULATION VERSUS VESICULATION." Cell 75(1): 123-133.
45. Zimmerberg, J. and M. M. Kozlov (2006). "How proteins produce cellular membrane curvature." Nature Reviews Molecular Cell Biology 7(1): 9-19.

The invention claimed is:

1. A method for forming a composition comprising a vesicle having a bilayer architecture having a tubular geometry comprising a lipid and an amphiphilic block copolymer, wherein the amphiphilic block copolymer is capable of undergoing self-assembly to form an architecture of a spherical geometry, the method comprising:
mixing in a pre-determined molar proportion of a solution of the amphiphilic block copolymer with the lipid in an organic solvent, wherein the pre-determined molar proportion of amphiphilic block copolymer to lipid is between 0.15:0.85 and 0.85:0.15;
evaporating the organic solvent after the mixing to obtain a lipid-polymer cake;
desiccating the lipid-polymer cake to obtain a dry thin film;
rehydrating the dry thin film in a hydrating solution to obtain an emulsion; and
allowing the composition to spontaneously self-assemble to the vesicle having the bilayer architecture, wherein the bilayer of the self-assembled vesicle encloses a volume having a tubular geometry in which the inner monolayer of the vesicle is enriched for the lipid and the outer monolayer of the vesicle is enriched for the amphiphilic block copolymer.

2. The method of claim 1, wherein the pre-determined proportion of amphiphilic block copolymer to lipid is 1:1.

3. The method of claim 1, wherein the organic solvent is selected from the group consisting of chloroform, ethanol, glycerol, tetrahydrofuran, dichloromethane, hexane, heptane, ethyl acetate, acetone, and a mixture thereof.

4. The method of claim 3, wherein the organic solvent contains a substance to be integrated in the bilayer architecture.

5. The method of claim 1, wherein the hydrating solution is selected from the group consisting of phosphate-buffered saline (PBS), 4-(2-hydroxyethyl)-1piperazineethanesulfonic acid (HEPES), Tris(hydroxymethyl)aminomethane (Tris), 3-(Nmorpholino)propanesulfonic acid (MOPS), acetate, water, and a mixture thereof.

6. The method of claim 1, wherein the hydrating solution further comprises a substance to be encapsulated by the inner layer of the bilayer architecture.

7. The method of claim 6, wherein the substance is water soluble or wherein the substance is lipid soluble.

8. The method of claim 7, wherein the substance is released from the composition,
   wherein the substance released from the composition is preferably bioactive or pharmaceutically active.

* * * * *